US008804122B2

(12) United States Patent
Chhibber et al.

(10) Patent No.: US 8,804,122 B2
(45) Date of Patent: Aug. 12, 2014

(54) SYSTEMS AND METHODS FOR DETERMINING A SURFACE PROFILE USING A PLURALITY OF LIGHT SOURCES

(75) Inventors: Rajeshwar Chhibber, San Jose, CA (US); Ashutosh Chhibbar, San Jose, CA (US); Shefali Sharma, Petaluma, CA (US)

(73) Assignee: Brightex Bio-Photonics LLC, San Jose, CA (US)

( * ) Notice: Subject to any disclaimer, the term of this patent is extended or adjusted under 35 U.S.C. 154(b) by 494 days.

(21) Appl. No.: 13/240,969

(22) Filed: Sep. 22, 2011

(65) Prior Publication Data

US 2013/0076932 A1  Mar. 28, 2013

(51) Int. Cl.
*G01J 4/00* (2006.01)
*G06K 9/46* (2006.01)
*G06K 9/00* (2006.01)
*A61B 5/00* (2006.01)
*G01N 21/21* (2006.01)

(52) U.S. Cl.
CPC .......... *G06K 9/4652* (2013.01); *G06K 9/00234* (2013.01); *G06T 2207/30088* (2013.01); *A61B 5/442* (2013.01); *G01N 21/21* (2013.01)
USPC ...................................................... 356/369

(58) Field of Classification Search
CPC .... A61B 5/442; A61B 5/0059; A61B 5/0064; A61B 5/441; A61B 5/0073; A61B 5/1077–5/1079; G06K 9/20–9/32; G06K 9/34–9/348; G06K 9/00221–9/00261; G01N 21/21; G06T 2207/30088; G01B 11/30–11/306
See application file for complete search history.

(56) References Cited

U.S. PATENT DOCUMENTS

| 4,151,512 A | 4/1979 | Riganati et al. |
| 4,186,378 A | 1/1980 | Moulton |
| 4,236,082 A | 11/1980 | Butler |
| 4,871,262 A | 10/1989 | Krauss et al. |
| 4,894,547 A | 1/1990 | Leffell et al. |
| 5,074,306 A | 12/1991 | Green et al. |
| 5,343,536 A | 8/1994 | Groh |
| 5,363,854 A | 11/1994 | Martens et al. |
| 5,631,975 A * | 5/1997 | Riglet et al. .................. 382/173 |
| 5,818,954 A | 10/1998 | Tomono et al. |

(Continued)

FOREIGN PATENT DOCUMENTS

WO   WO 90/13091 A1   11/1990

OTHER PUBLICATIONS

Brightex Bio-Photonics, IPRP, PCT/US2011/031065, Oct. 11, 2012, 11 pgs.

(Continued)

*Primary Examiner* — Gregory J Toatley
*Assistant Examiner* — Juan D Valentin, II
(74) *Attorney, Agent, or Firm* — Ward & Zinna, LLC

(57) ABSTRACT

A method for determining a surface profile of subject's skin includes illuminating the subject with light from a plurality of light sources. The plurality of light sources having distinct colors is configured to illuminate the subject from distinct locations. A multi-color image of the subject is obtained. The multi-color image includes respective values corresponding to respective intensities of light of respective colors for each region of the subject. A surface profile of the subject is determined in accordance with the respective values corresponding to the respective intensities of light of the respective colors.

16 Claims, 19 Drawing Sheets
(3 of 19 Drawing Sheet(s) Filed in Color)

(56) References Cited

U.S. PATENT DOCUMENTS

| | | | |
|---|---|---|---|
| 5,836,872 | A | 11/1998 | Kenet et al. |
| 5,862,247 | A | 1/1999 | Fisun et al. |
| 6,021,344 | A | 2/2000 | Lui et al. |
| 6,032,071 | A | 2/2000 | Binder |
| 6,061,463 | A | 5/2000 | Metz et al. |
| 6,069,689 | A | 5/2000 | Zeng et al. |
| 6,081,612 | A | 6/2000 | Gutkowicz-Krusin et al. |
| 6,122,042 | A * | 9/2000 | Wunderman et al. ......... 356/343 |
| 6,141,434 | A | 10/2000 | Christian et al. |
| 6,317,624 | B1 | 11/2001 | Kollias et al. |
| 6,475,153 | B1 | 11/2002 | Khair et al. |
| 6,533,729 | B1 | 3/2003 | Khair et al. |
| 6,556,708 | B1 | 4/2003 | Christian et al. |
| 6,571,003 | B1 | 5/2003 | Hillebrand et al. |
| 6,587,711 | B1 | 7/2003 | Alfano et al. |
| 6,611,622 | B1 | 8/2003 | Krumm |
| 6,763,262 | B2 | 7/2004 | Hohla et al. |
| 6,782,307 | B2 | 8/2004 | Wilmott et al. |
| 6,907,138 | B1 | 6/2005 | Hoffman et al. |
| 7,217,266 | B2 | 5/2007 | Anderson et al. |
| 7,233,693 | B2 | 6/2007 | Momma |
| 7,289,211 | B1 | 10/2007 | Walsh, Jr. et al. |
| 7,349,857 | B2 | 3/2008 | Manzo |
| 7,369,692 | B2 | 5/2008 | Shirai et al. |
| 7,454,046 | B2 | 11/2008 | Chhibber et al. |
| 7,460,248 | B2 | 12/2008 | Kurtz et al. |
| 7,477,767 | B2 | 1/2009 | Chhibber et al. |
| 7,627,151 | B2 | 12/2009 | Rowe |
| 7,840,064 | B2 | 11/2010 | Chhibber et al. |
| 8,131,029 | B2 | 3/2012 | Chhibber et al. |
| 2002/0090133 | A1* | 7/2002 | Kim et al. .................... 382/164 |
| 2003/0086599 | A1* | 5/2003 | Armato et al. ................ 382/131 |
| 2003/0223083 | A1 | 12/2003 | Geng |
| 2004/0071366 | A1* | 4/2004 | Zhang et al. .................. 382/284 |
| 2004/0111031 | A1 | 6/2004 | Alfano et al. |
| 2004/0125996 | A1 | 7/2004 | Eddowes et al. |
| 2004/0179719 | A1 | 9/2004 | Chen et al. |
| 2004/0249274 | A1 | 12/2004 | Yaroslavsky et al. |
| 2005/0008199 | A1 | 1/2005 | Dong et al. |
| 2005/0046830 | A1 | 3/2005 | Karp et al. |
| 2005/0195316 | A1 | 9/2005 | Kollias et al. |
| 2006/0092315 | A1 | 5/2006 | Payonk et al. |
| 2006/0182323 | A1 | 8/2006 | Kollias et al. |
| 2007/0002479 | A1 | 1/2007 | Menke et al. |
| 2007/0004972 | A1 | 1/2007 | Cole et al. |
| 2007/0064978 | A1 | 3/2007 | Chhibber et al. |
| 2007/0064979 | A1 | 3/2007 | Chhibber et al. |
| 2007/0092160 | A1* | 4/2007 | Fujii et al. .................... 382/286 |
| 2008/0051773 | A1 | 2/2008 | Ivanov et al. |
| 2008/0212894 | A1 | 9/2008 | Demirli et al. |
| 2009/0136101 | A1 | 5/2009 | Chhibber et al. |
| 2009/0141956 | A1 | 6/2009 | Chhibber et al. |
| 2009/0196475 | A1 | 8/2009 | Demirli et al. |
| 2009/0226049 | A1* | 9/2009 | Debevec et al. .............. 382/118 |
| 2010/0309300 | A1 | 12/2010 | Chhibber et al. |
| 2010/0316296 | A1 | 12/2010 | Chhibber et al. |

OTHER PUBLICATIONS

Anonymous, *Build Your Own 3D Scanner w/Structured Light*, Nov. 23, 2009, 7 pgs.

Anonymous, *Stereo Accuracy and Error Modeling*, Point Grey Research Inc., Apr. 19, 2004, 3 pgs.

Basset, *Application of texture image analysis for the classification of bovine meat*, Food Chemistry 69, 2000, pp. 437-445.

Blanz, *A Morphable Model for the Synthesis of 3D Faces*, SIGGRAPH '99, Los Angeles CA, 1999, pp. 187-194.

Brightex Bio-Photonics LLC, International Search Report and Written Opinion, PCT/US2011/031065 dated Jun. 20, 2011, 11 pgs.

Brightex Bio-Photonics LLC, International Search Report and Written Opinion, PCT/US2006/036696, Nov. 6, 2007, 5 pgs.

Brightex Bio-Photonics LLC, International Search Report and Written Opinion, PCT/US2010/028617, May 20, 2010, 7 pgs.

Fulton, *Utilizing the Ultraviolet (UV Detect) Camera to Enhance the Appearance of Photodamage and Other Skin Conditions*, American Society for Dermatologic Surgery, 1997, pp. 163-169.

Hsu, *Face Detection in Color Images*, IEEE Transactions on Pattern Analysis and Machine Intelligence, vol. 24, No. 5, May 2002, pp. 696-706.

Kollias, *Optical Non-Invasive Approaches to Diagnosis of Skin Diseases*, JID Symposium Proceedings, 2002, pp. 64-75.

Liangen, *Human Skin Surface Evaluation by Image Processing*, SPIE vol. 5254, 3rd Int'l Conference on Photonics and Imaging in Biology and Medicine, Bellingham WA, 2003, pp. 362-367.

Rosco color filter technical data sheet, 2001, 2 pgs.

Sandby-Moller, *Influence of epidermal thickness, pigmentation and redness on skin autofluorescence*, American Society of Photobiology, Jun. 2003, pp. 1-9.

Sboner, *Clinical validation of an automated system for supporting the early diagnosis of melanoma*, Skin Research and Technology, vol. 10, 2004, pp. 184-192.

Zeng, *Autofluorescence properties of skin and application in dermatology*, Proceedings of SPIE, Bol. 4224, 2000, pp. 366-373.

Zhang, *3-D Face Structure Extraction and Recognition From Images Using 3-D Morphing and Distance Mapping*, IEEE Transactions on Image Processing, vol. 11, No. 11, Nov. 2002, 1249-1259.

\* cited by examiner

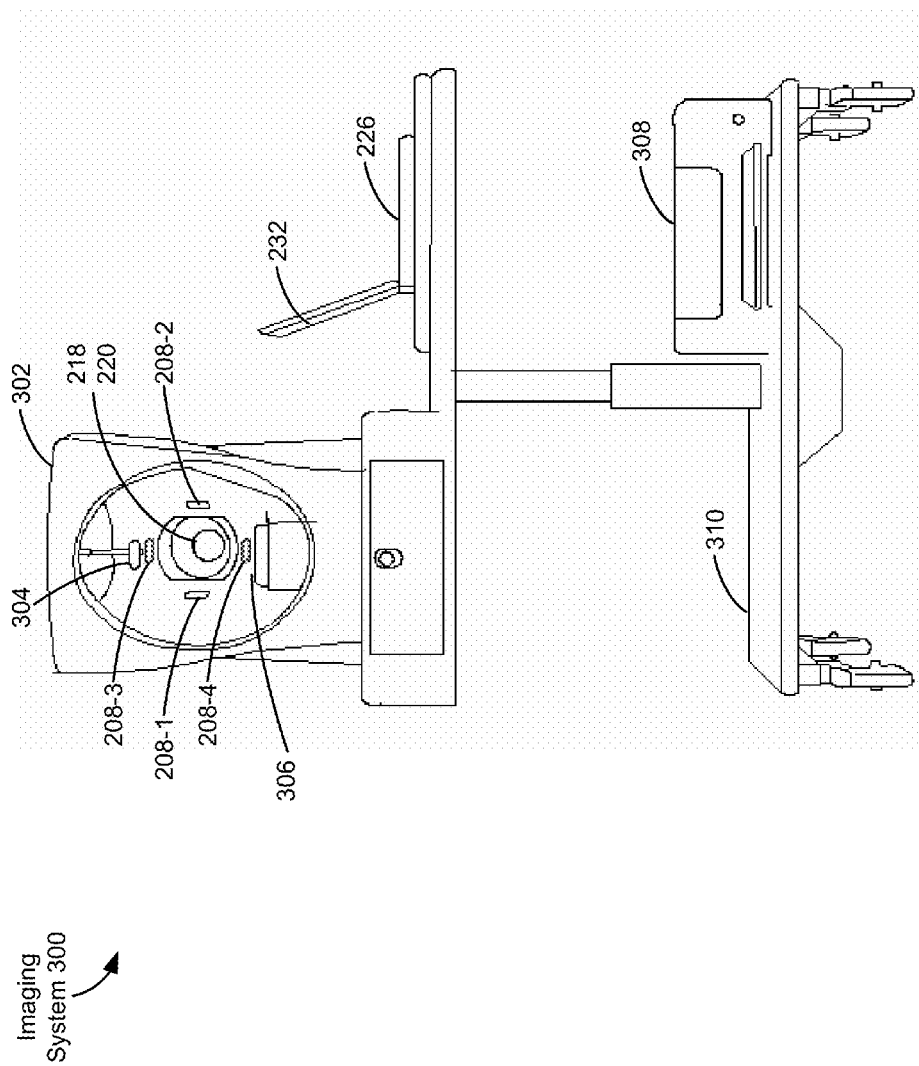

600

---

602 Illuminate a subject with light from a plurality of light sources. The plurality of light sources having distinct colors is configured to illuminate the subject from distinct locations

604 The plurality of light sources emits light of respective colors that have distinct spectra

---

606 Obtain a multi-color image of the subject. The multi-color image includes respective values corresponding to respective intensities of light of respective colors for each region of the subject

608 Obtaining the multi-color image includes: obtaining a parallel-polarization image of the subject; obtaining a cross-polarization image of the subject; and subtracting the cross-polarization image of the subject from the parallel-polarization image of the subject to produce the multi-color image of the subject

---

(A)

Figure 6A

SYSTEMS AND METHODS FOR DETERMINING A SURFACE PROFILE USING A PLURALITY OF LIGHT SOURCES

RELATED APPLICATIONS

This application is related to U.S. patent application Ser. No. 13/078,834, filed Apr. 1, 2011, entitled "Methods and Systems for Imaging and Modeling Skin Using Polarized Lighting," which claims priority to U.S. Provisional Application Ser. No. 61/320,627, filed Apr. 2, 2010, entitled "Methods and Systems for Imaging and Modeling Skin Using Polarized Lighting," and is a continuation-in-part of U.S. patent application Ser. No. 12/731,072, filed Mar. 24, 2010, entitled "Methods and Systems for Imaging Skin Using Polarized Lighting," which claims priority to U.S. Provisional Application Ser. No. 61/164,356, filed Mar. 27, 2009, entitled "Methods and Systems for Imaging Skin Using Polarized Lighting." All of these applications are incorporated by reference herein in their entirety.

TECHNICAL FIELD

The disclosed embodiments relate generally to imaging skin, and more particularly, to determining a surface profile of skin using a plurality of light sources.

BACKGROUND

Surface profiles of subjects' skin have potential applications in dermatology and cosmetics, among other fields. Obtaining high-quality surface profiles, however, presents significant technical challenges. For example, skin pigmentations can interfere with imaging fine features on the skin (e.g., wrinkles). In addition, a subject's motion can interfere with accurate determination of the surface profile.

SUMMARY

Accordingly, there is a need for systems that can rapidly obtain high-quality surface profiles. The above deficiencies and other related problems are addressed by the systems and methods described herein. In some embodiments, a method includes illuminating a subject with light from a plurality of light sources. The plurality of light sources having distinct colors is configured to illuminate the subject from distinct locations. The method also includes obtaining a multi-color image of the subject. The multi-color image includes respective values corresponding to respective intensities of light of respective colors for each region of the subject. The method furthermore includes determining a surface profile of the subject in accordance with the respective values corresponding to the respective intensities of light of the respective colors.

In some embodiments, an optical system includes a plurality of light sources for illuminating a subject. The plurality of light sources having distinct colors is configured to illuminate the subject from distinct locations. The optical system also includes an optical image sensor used for obtaining a multi-color image of the subject. The multi-color image includes respective values corresponding to respective intensities of light of respective colors for each region of the subject. The optical system furthermore includes one or more processors coupled with the optical image sensor, and memory storing one or more programs for execution by the one or more processors. The one or more programs include instructions for determining a surface profile of the subject in accordance with the respective values corresponding to the respective intensities of light of the respective colors.

In some embodiments, a non-transitory computer readable storage medium stores one or more programs for execution by one or more processors of a computer system. The one or more programs include instructions for obtaining a multi-color image of a subject illuminated with a plurality of light sources that has distinct colors and is configured to illuminate the subject from distinct locations. The multi-color image includes respective values corresponding to respective intensities of light of respective colors for each region of the subject. The one or more programs include instructions for determining a surface profile of the subject in accordance with the respective values corresponding to the respective intensities of light of the respective colors.

Thus, systems for determining surface profiles of subjects' skin are provided with more efficient methods for surface profiling based on illumination with a plurality of light sources, thereby increasing the speed, quality, accuracy, and details of surface profiles.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2C are block diagrams of imaging systems for imaging skin in accordance with some embodiments.

FIGS. 6A-6B are flow diagrams illustrating a method of determining a surface profile of skin in accordance with some embodiments.

Like reference numerals refer to corresponding parts throughout the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the present inventions. However, it will be apparent to one of ordinary skill in the art that the present inventions may be practiced without these specific details. In other instances, well-known methods, procedures, components, and circuits have not been described in detail so as not to unnecessarily obscure aspects of the embodiments. In addition, it should be noted that at least some of the drawings are not drawn to scale.

It will also be understood that, although the terms first, second, etc. may be used herein to describe various elements, these elements should not be limited by these terms. These terms are only used to distinguish one element from another. For example, a first image could be termed a second image, and, similarly, a second image could be termed a first image, without departing from the scope of the present invention. The first image and the second image are both images, but they are not the same image. Similarly, a first axis could be termed a second axis, and a second axis could be termed a first axis.

As used herein, "light of a [first, second, third, or fourth] color" refers to electromagnetic radiation that can be visually perceived by humans. Light of a color typically has a wavelength ranging from approximately 400 nm to 700 nm. However, it should be noted that light of a color may be accompanied by ultraviolet and/or infrared light.

Figure 1A:
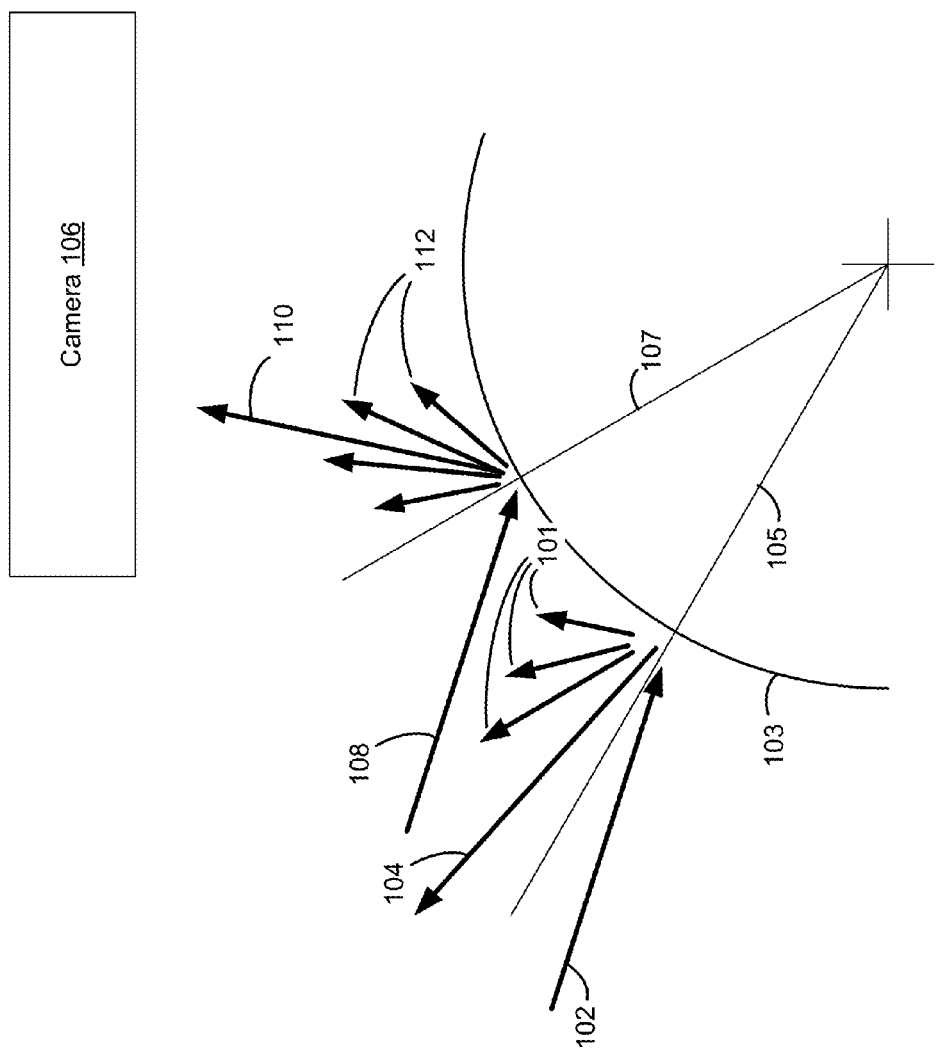
FIGS. 1A-1D illustrate light incident on and reflected from skin in accordance with some embodiments.

FIG. 1A is a schematic diagram illustrating light incident on and reflected from skin 103 in accordance with some embodiments. In FIG. 1A, a feature of the skin 103 is illustrated with an arc, and light from a light source is illustrated with rays 102 and 108. The rays 102 and 108 impinge on the skin 103 at distinct locations. The ray 102 impinges on the skin 103 at a location where the surface normal is represented by a line 105, and the ray 108 impinges on the skin 103 at a location where the surface normal is represented by a line 107. After the ray 102 impinges on the skin 103, the ray 102 is reflected. The reflection of the ray 102 includes specularly reflected light 104 and diffusely reflected light, some components of which are represented by rays 101. Similarly, after the ray 108 impinges on the skin 103, the ray 108 is reflected. The reflection of the ray 108 includes specularly reflected light 110 and diffusely reflected light, some components of which are represented by rays 112.

Specularly reflected light has a particular direction with respect to the incoming light. Specifically, an angle between the incoming light and the surface normal of the surface the incoming light impinges on is the same as an angle between the specularly reflected light and the surface normal of the surface. Thus, when specular reflection (e.g., the ray 110) is observed from a region of the skin 103 by a camera 106, the surface normal of the region of the skin 103 which the incoming light impinges on may be identified based on a direction of the incoming light (e.g., the ray 108). For example, when a subject is illuminated with light incoming at a 60° degree angle from a line extending from the subject to the camera 106, the surface normal of a region of the subject's skin where the specular reflection is detected is approximately 30° degrees from the line extending from the subject to the camera 106. In some embodiments, the surface normal of the region of the skin 103 is determined based on the direction of the incoming light and a location of the region of the skin 103 with respect to the camera 106.

In comparison, diffusely reflected light is distributed in a range of directions. An angular distribution of diffusely reflected light is often modeled as a Lambertian distribution. A Lambertian distribution refers to a distribution of light where a radiance of the reflected light remains the same regardless of an angle of the reflected light, although the intensity of the reflected light varies in accordance with the angle of the reflected light. Thus, it is more challenging to determine an angle of a skin surface solely based on the radiance of the diffusely reflected light. Therefore, in some embodiments, the diffusely reflected light is removed prior to determining a surface profile.

Figure 1B:
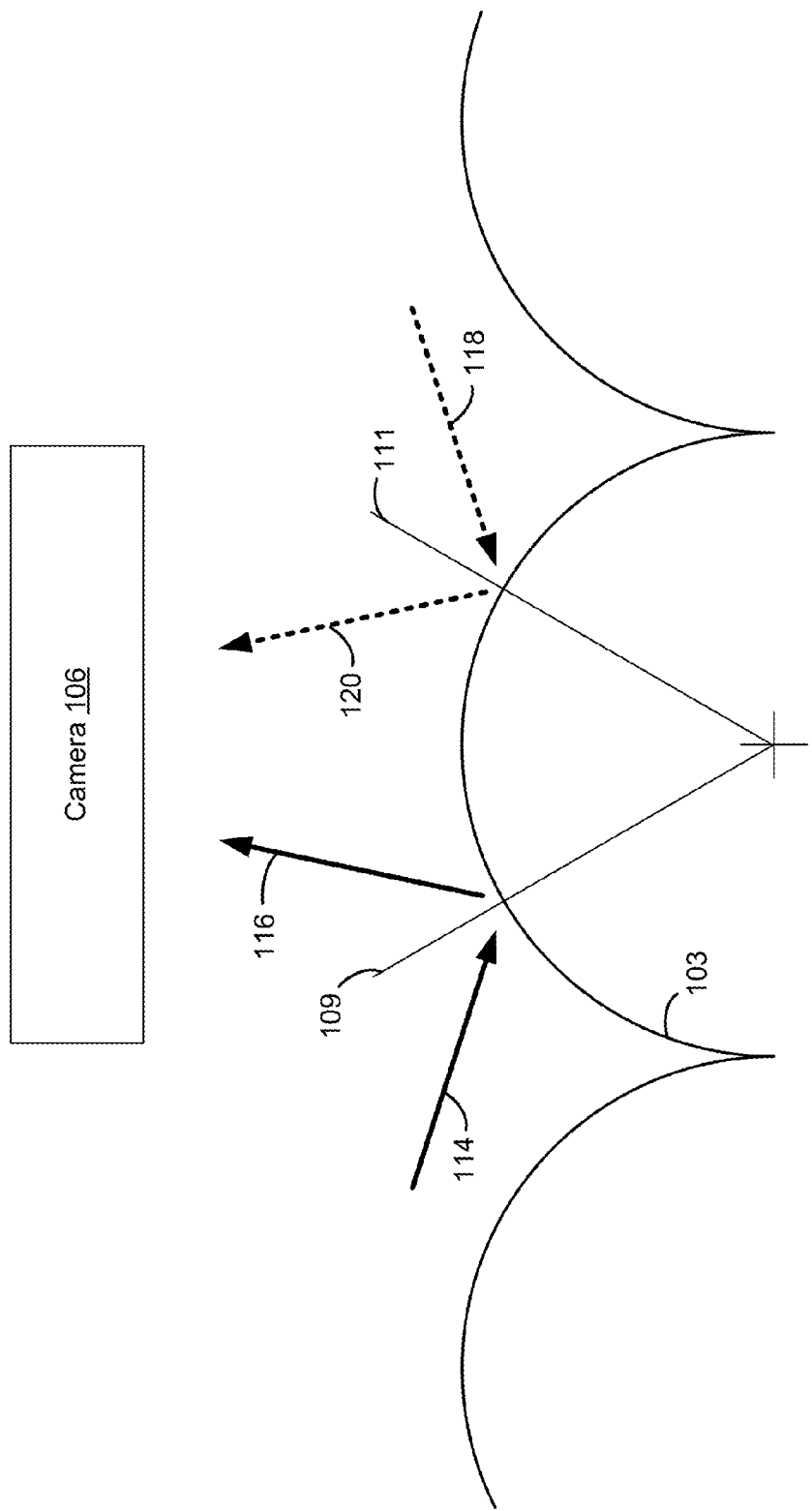

FIG. 1B is a schematic diagram illustrating light of two different colors incident on and reflected from the skin 103 in accordance with some embodiments. In FIG. 1B, features (e.g., wrinkles and/or bumps) of the skin 103 are illustrated with arcs. Incoming light of a first color is illustrated with a ray 114, and incoming light of a second color is illustrated with a ray 118. The ray 114 impinges on the skin 103 at a location where the surface normal is represented by a line 109, and the ray 118 impinges on the skin 103 at a location where the surface normal is represented by line 111. After the ray 114 impinges on the skin 103, the ray 114 is reflected. The reflection of the ray 114 includes specularly reflected light 116 and diffusely reflected light (not shown). Similarly, after the ray 118 impinges on the skin 103, the ray 118 is reflected. The reflection of the ray 118 includes specularly reflected light 120 and diffusely reflected light (not shown). Based on the specular reflection of light of the first color at a first region of the skin 103 where the ray 114 impinges, the surface normal 109 of the first region of the skin 103 can be identified based on a predefined direction of the incoming light of the first color (e.g., the ray 114). Similarly, based on the specular reflection of light of the second color at a second region of the skin 103 where the ray 118 impinges, the surface normal 111 of the second region of the skin 103 may be identified based on a predefined direction of the incoming light of the second color (e.g., the ray 118).

Figure 1C:
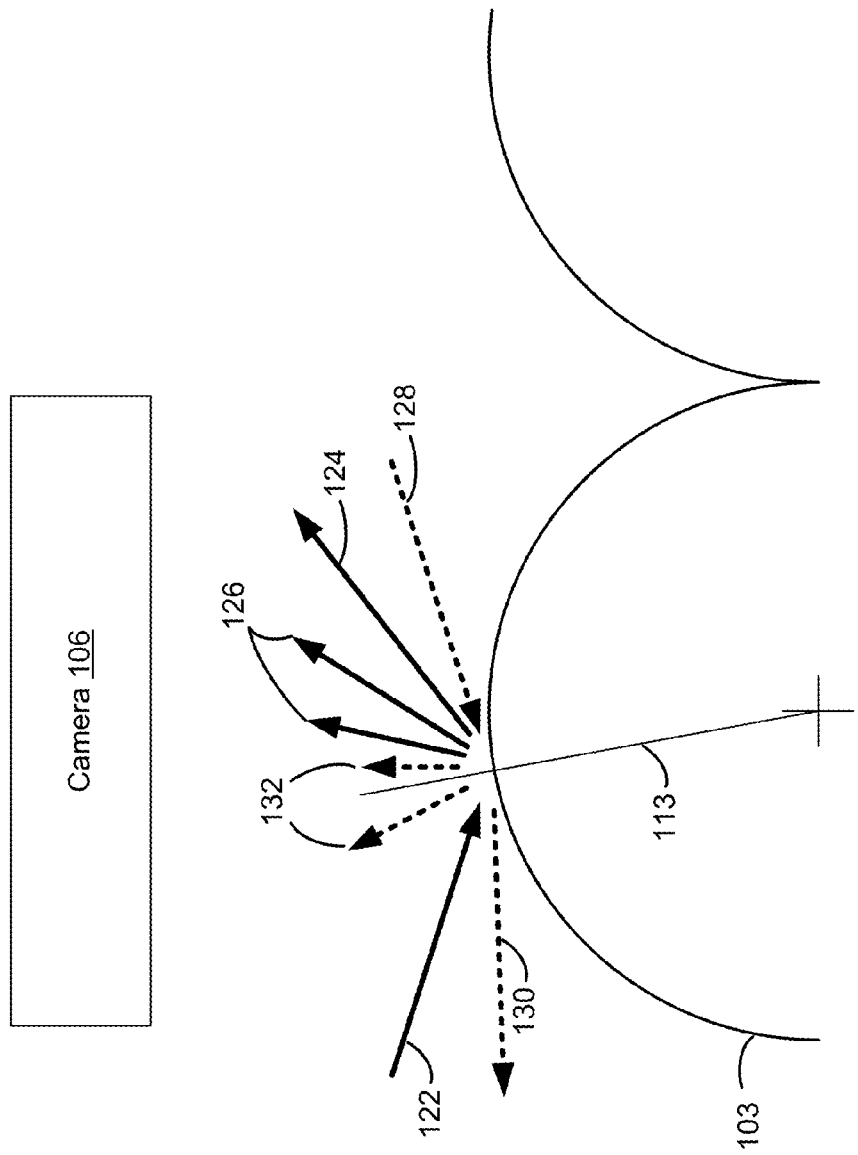

FIG. 1C is a schematic diagram illustrating light of two different colors incident on and reflected from the skin 103 in accordance with some embodiments. In FIG. 1C, features of the skin 103 are illustrated with arcs. Incoming light of a first color is illustrated with a ray 122, and incoming light of a second color is illustrated with a ray 128. The rays 122 and 128 impinge on the skin 103 at a location where the surface normal is represented by a line 113. After the ray 122 impinges on the skin 103, the ray 122 is reflected. The reflection of the ray 122 includes specularly reflected light 124 and diffusely reflected light, some components of which are represented by rays 126. Similarly, after the ray 128 impinges on the skin 103, the ray 128 is reflected. The reflection of the ray 128 includes specularly reflected light 130 and diffusely reflected light, some components of which are represented by rays 132. The rays 124 and 130 are not detected by the camera 106. However, the intensity of diffusely reflected light of multiple colors (e.g., the rays 126 and 132) can be used to determine the surface normal of a region of the skin 103 where the rays 122 and 128 impinge. In particular, a respective intensity of light for each color is used in determining the surface normal of the region of the skin 103.

Figure 1D:
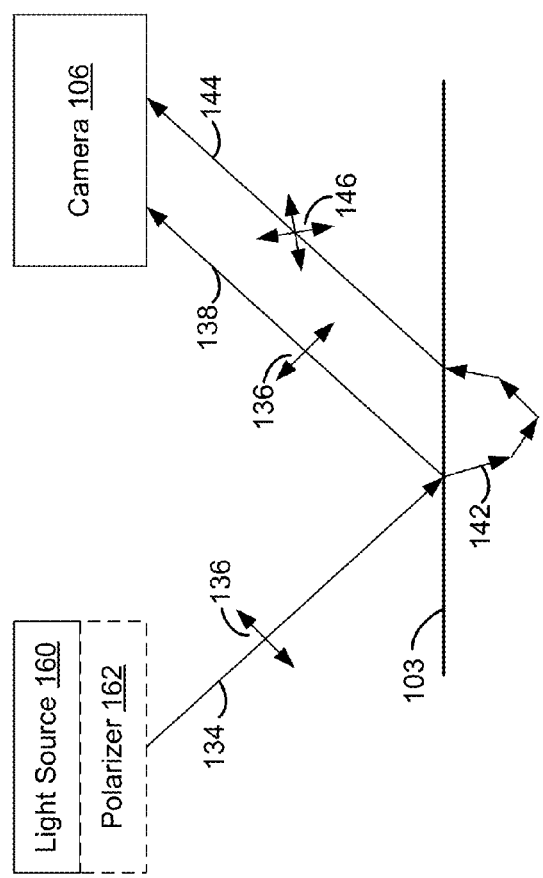

FIG. 1D is a schematic diagram illustrating light incident on and reflected from skin 103 in accordance with some embodiments. In some embodiments, a light source 160 is configured to emit polarized light (e.g., a laser or polarized light-emitting diode). In some other embodiments, the light source 160 is configured to emit light of mixed polarization (or non-polarized light), and a polarizer 162 (e.g., a linear polarizer) is used to transmit light of a particular polarization. Light 134 is typically linearly polarized (e.g., polarization 136 is a linear polarization).

Light 138 is reflected from the surface of the skin 103 and detected by a camera (e.g., a digital camera) 106. The light 138 reflected from the surface of the skin 103 has the same polarization 136 as the incident light 134 and thus is also linearly polarized.

However, not all of the incident light 134 is reflected from the surface of the skin 103. A portion 142 of the incident light 134 penetrates the skin 103, and is scattered one or more times before being reflected. (For simplicity, FIG. 1D shows the portion 142 of the incident light 134 following a single path within the skin 103 before being reflected as light 144. In reality, the portion 142 of the incident light 134 follows various paths within the skin 103 before being reflected.) The light 144 reflected from beneath the surface of the skin 103 has a polarization (e.g., an elliptical polarization) 146 distinct from the polarization 136 of the light 138 reflected from the surface of the skin 103. Typically, the polarization 146 of the light 144 is random.

The camera 106 thus receives partially polarized light: at least a portion of the received light includes the light 138, of the polarization 136, reflected from the surface of the skin 103, and the light 144, of random polarization 146, reflected from beneath the surface of the skin 103.

In some embodiments, the camera 106 is equipped with a polarizer which may be configured (e.g., by rotating the polarizer) to (1) admit only light having the polarization 136, such that all other polarizations are rejected, (2) reject all light having the polarization 136, such that admitted light is polarized perpendicular to the polarization 136, or (3) admit partially both light having the polarization 136 and light having a polarization perpendicular to the polarization 136. In the first case, an image taken by the camera 106 corresponds to the light 138 reflected from the surface of the skin 103 and is thus an image of the surface of the skin 103. In the second case, an image taken by the camera 106 corresponds to the light 144 reflected from a depth beneath the surface of the skin 103. The depth may vary from approximately 350 microns for very dark skin (e.g., Type 6 skin on the Fitzpatrick scale) to approximately 3 mm for very fair skin (e.g., Type 1 skin on the Fitzpatrick scale). The image in the second case is thus a sub-surface image of the skin 103. In the third case, an image taken by the camera 106 corresponds to light reflected from both the surface and from varying depths beneath the surface of the skin 103 and thus can be considered a combination of surface and sub-surface skin images.

Figure 1E:
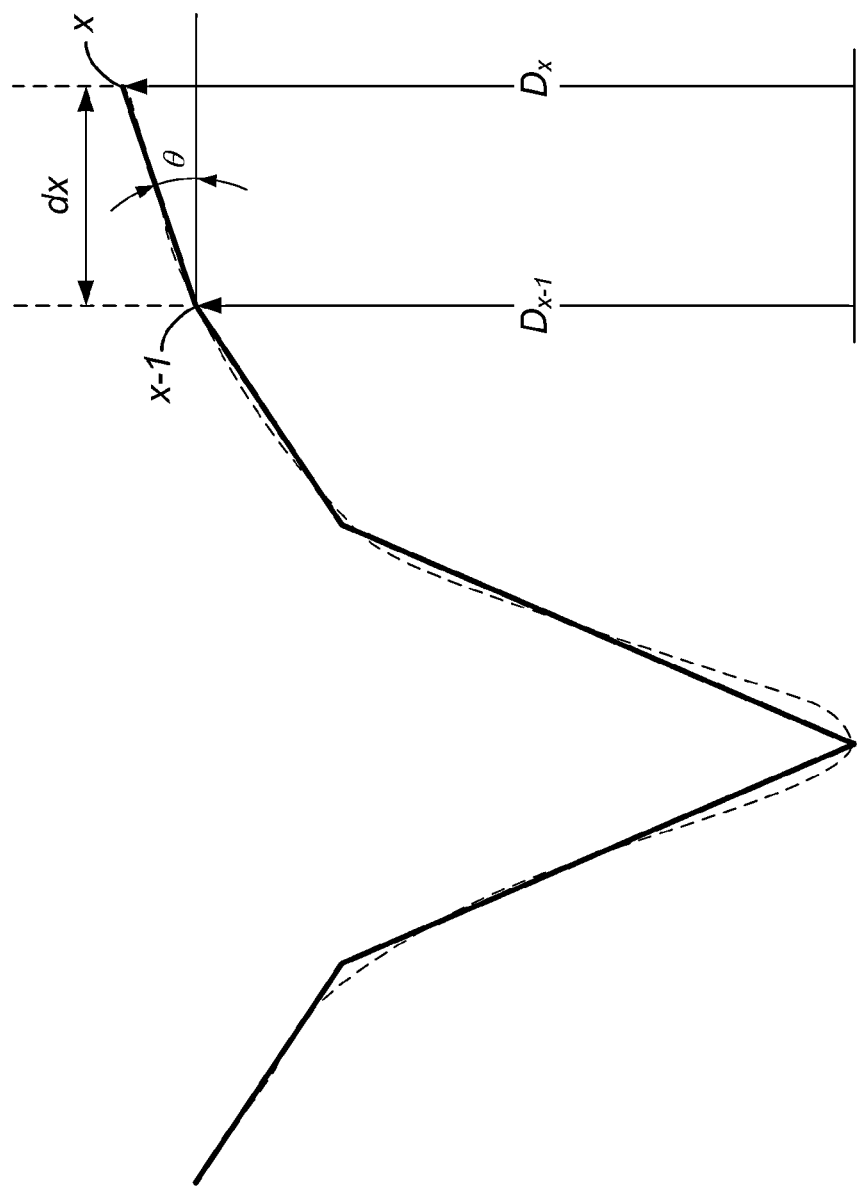
FIG. 1E illustrates a cross-sectional view of a surface of a subject's skin in accordance with some embodiments.

FIG. 1E illustrates an exemplary cross-sectional view of a surface profile of a subject's skin in accordance with some embodiments. In FIG. 1E, the surface profile is illustrated with a dashed line. The surface profile may be representation of a pore in the subject's skin. Also shown in FIG. 1E is a combination of straight solid lines that models the surface profile. A joint between two straight lines is called herein a node. The combination of solid lines illustrated in FIG. 1E includes at least a node x−1 and a node x, which are separated by a horizontal distance dx. The height (or displacement or distance) of the node x−1, relative to a reference point, is $D_{x-1}$, and the height (or displacement) of the node x, relative to the reference point, is $D_x$. In some embodiments, the height (or displacement) of the node x is determined at least partially from the height (or displacement) of the node x−1 and an angle (or direction/orientation) of the region of the skin 103. For example, the following equation may be used to determine the height (or displacement) of the node x:

$$D_x = D_{x-1} + dx \cdot \tan \theta \quad \text{(Eq. 1)}$$

where $D_x$ is the displacement of the node x, $D_{x-1}$ is the displacement of the node x−1, dx is a horizontal distance between the node $D_{x-1}$ and the node $D_x$, and θ is the angle of the region of the skin 103 between the node $D_{x-1}$ and the node $D_x$ (e.g., an angle between a surface normal of the region and a first reference axis, such as a vertical axis, or an angle between a line extending from the node $D_{x-1}$ to the node $D_x$ and a second reference axis, such as a horizontal axis shown in FIG. 1E).

Figure 1F:
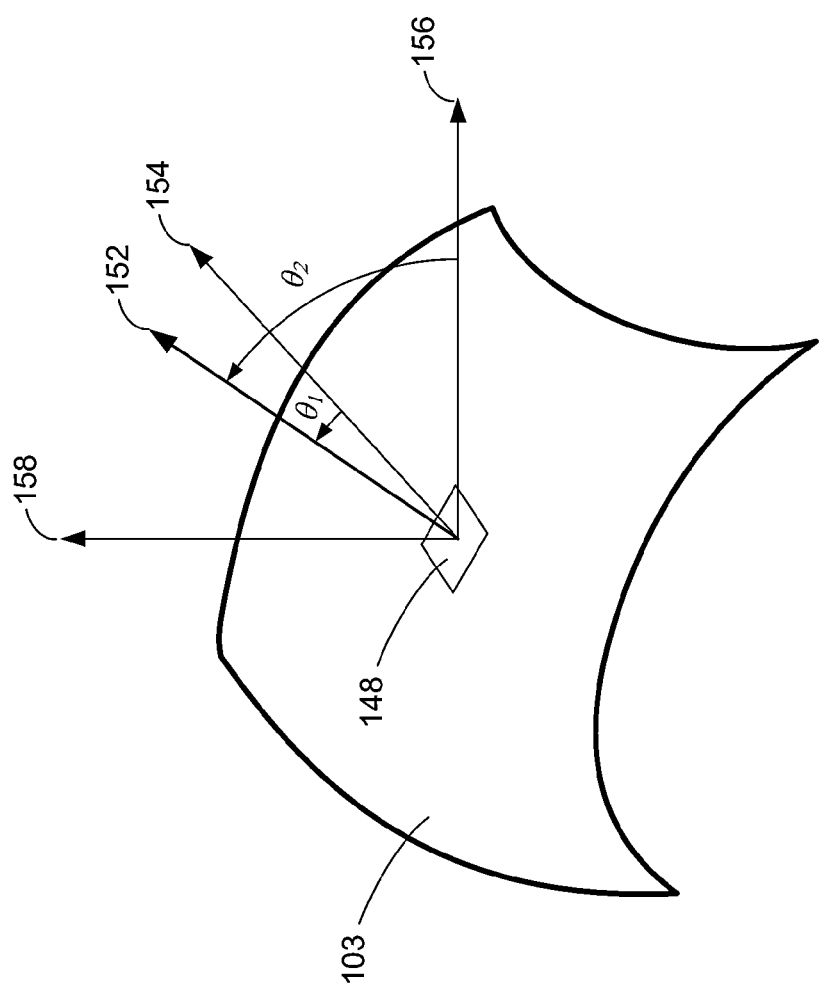
FIGS. 1F-1G illustrates a respective surface of a subject in accordance with some embodiments.
Figure 1G:
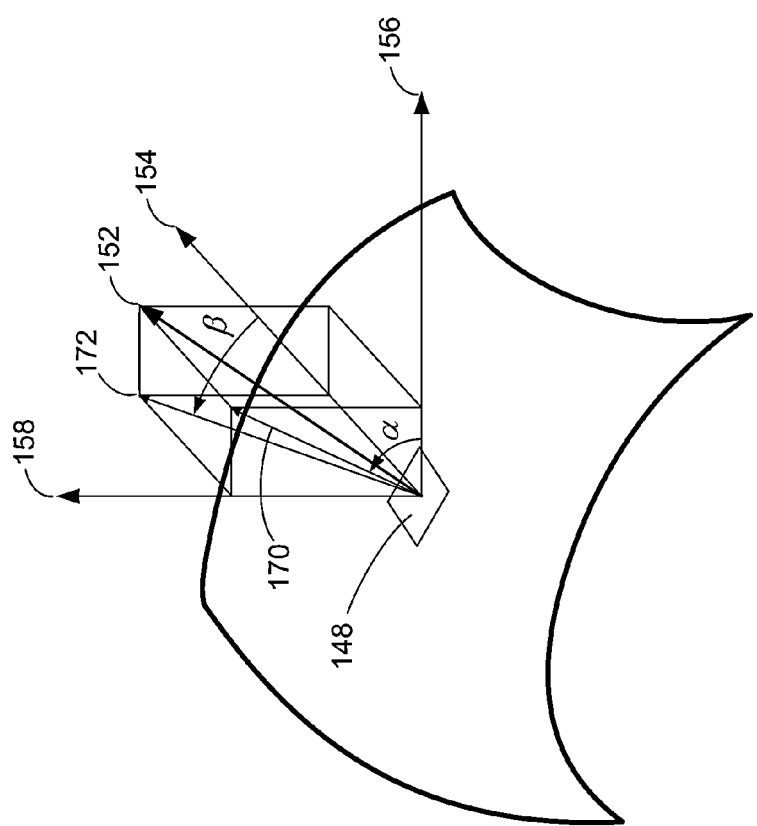

FIGS. 1F-1G illustrate a respective surface of the skin 103 in accordance with some embodiments. It is well known that a small region 148 of the skin 103 can be modeled as a flat surface. The direction (or angle or orientation) of the region 148 is represented by a surface normal 152 of the region 148.

In FIG. 1F, the surface normal 152 of the region 148 is characterized by angles between the surface normal 152 and predefined axes. In a Cartesian coordinate system that includes three mutually perpendicular axes (e.g., axes 154, 156, and 158), the direction of the surface normal 152 may be characterized using $\cos \theta_1$ and $\cos \theta_2$ values (or the angles $\theta_1$ and $\theta_2$), where $\theta_1$ is the angle between the surface normal 152 and a first predefined axis 154 and $\theta_2$ is the angle between the surface normal 152 and a second predefined axis 156. For illustrative purposes only, the axis 156 is called herein a horizontal axis (e.g., an axis that extends from the left side to the right side), and the axis 154 is called herein a vertical axis (e.g., an axis that extends from the bottom of a subject to the top of the subject). The axis 158 extends from the back side of the subject toward the front side of the subject.

Alternatively, as shown in FIG. 1G, the surface normal 152 of the region 148 is characterized by an angle α between a projection 170 of the surface normal 152 (on a plane formed by the predefined axes 156 and 158) and a first predefined axis 156, and an angle β between a projection 172 of the surface normal 152 (on a plane formed by the predefined axes 154 and 158) and a second predefined axis 154. The angle α is called herein a horizontal tilt, indicating whether the region 148 is tilted toward the left side or right side of the subject, and the angle β is called herein a vertical tilt, indicating whether the region 148 is tilted toward the top or bottom of the subject. When the region is not tilted in any direction, each of the angles α and β is 90°.

However, it should be noted that the surface normal 152 (and an angle or orientation of the region 148) may be characterized based on any of other conventions well known in the art.

Figure 2A:
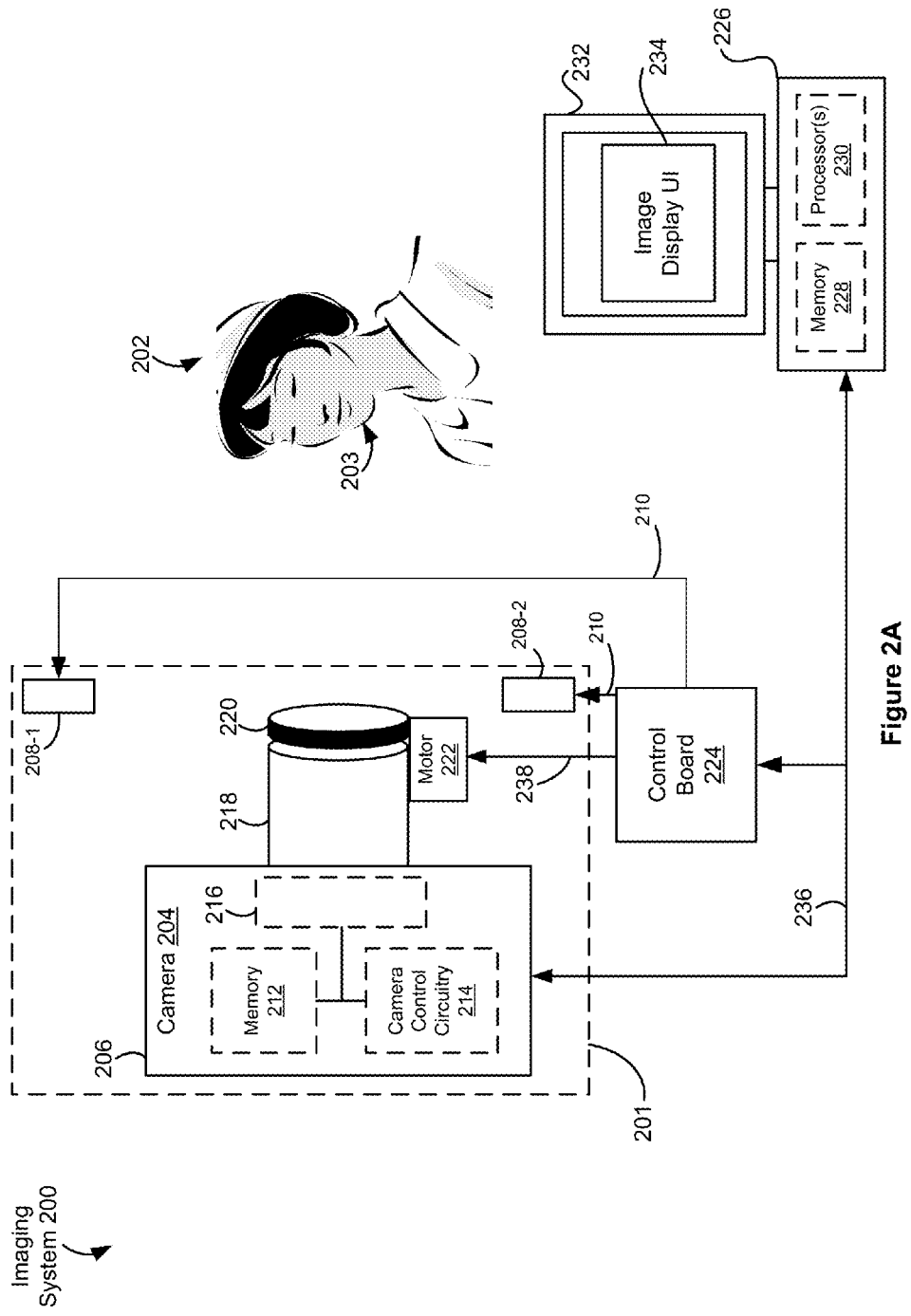

FIG. 2A is a block diagram of an imaging system 200 for imaging skin 203 of a subject 202 in accordance with some embodiments. The system 200 images the skin 203 in accordance with the physical principles illustrated in FIGS. 1A-1D. While the system 200 is illustrated as imaging human facial skin, in some embodiments the system 200 may be used to image skin of another body part, animal skin, or any type of hair as well as skin. In the system 200, an imaging apparatus 201 includes a camera (e.g., a digital camera) 204. The camera 204, which is an example of a camera 106 (FIG. 1), includes a photodetector 216 to acquire images of the subject 202, a non-transitory computer readable storage medium 212 to store acquired images, and camera control circuitry 214 (e.g., one or more processors) to control acquisition and storage of the images. The photodetector 216, memory 212, and control circuitry 214 are typically contained in a housing 206 of the camera 204. In some embodiments, the photodetector 216 comprises an array of charge-coupled devices (CCD), charge-injection devices (CID), and/or CMOS devices. In some embodiments, the photodetector 216 includes 5 to 15 megapixels. However, the photodetector 216 may include more or fewer pixels. In some embodiments, each pixel includes three sub-pixels corresponding to three distinct color channels (e.g., red, green, and blue, or alternatively, a set of colors associated with another color space). In some embodiments, the photodetector 216 is rotatable to provide a variable aspect ratio for acquired images. Rotation of the photodetector 216 is controlled, for example, by the control circuitry 214.

The system 200 includes one or more light sources 208 (hereinafter, "light sources 208") to illuminate the subject 202. The light sources 208 are examples of the light source 160, and in some cases, include polarizer 162 (FIG. 1D). In some embodiments, at least one of the light sources 208 is configured to emit polarized light (e.g., a laser or polarized LED). In some embodiments, at least one of the light sources 208 is coupled with a polarizer to polarize the light emitted by at least the one light source. As used herein, polarized light of a light source refers to at least one of: light polarized as emitted by the light source 208 and light polarized by an optical component (e.g., a polarizer) from non-polarized light emitted by the light source.

In some embodiments, the light sources 208 are coupled to the camera housing 206. For example, the light sources 208 are affixed to the camera housing 206 or integrated into the camera housing 206. Alternatively, the light sources 208 may be physically separated from the camera 204. In some embodiments, the light sources 208 include one or more flash bulbs, one or more light-emitting diodes (LEDs), or one or more fluorescent high-temperature white-light sources. In some embodiments, when the light sources 208 include one or more light sources, such as polarized LEDs, that are configured to emit polarized light, the system do not include separate polarizers. In some embodiments, when the system includes polarizers, the polarizers include one or more linear polarizers. In some embodiments, the polarizers are fixed, such that the polarization they provide is not adjustable. A polarizer may be mounted on a respective light source 208 or otherwise arranged such that it polarizes light from the light source 208 that is incident on the subject 202.

Each of the light sources 208 is located to illuminate the subject 202 from a distinct location (e.g., the light source 208-1 is located to illuminate the subject 202 from the top and the light source 208-2 is located to illuminate the subject 202 from the bottom; alternatively or additionally, a light source located to illuminate the subject 202 from one side and a light source located to illuminate the subject 202 from the opposite side may be used).

The system 200 includes a plurality of light sources 208, including a first light source 208-1 of a first color and a second light source 208-2 of a second color distinct from the first color. In some embodiments, at least one of the light sources 208 is configured to emit light of a respective color (e.g., an LED configured to emit red, green, blue, orange, or yellow light). In some embodiments, at least one of the light sources 208 includes a white light source (e.g., an incandescent light bulb, a xenon lamp, a white-light LED, etc.) and a color filter (e.g., red, green, blue, orange, or yellow filter, etc.).

When at least one of the light sources 208 (or its combination with a polarizer) is configured to provide polarized light, multiple light sources 208 are typically configured to provide light of the same polarization. For example, when the first light source 208-1 and the second light source 208-2 are both configured to provide polarized light, the polarization of light provided by the first light source 208-1 is the same as the polarization of light provided by the second light source 208-2.

In some embodiments, the light sources 208 are coupled to the control board 224 via one or more signal lines 210. In some embodiments, the light sources 208 include electrical circuitry to receive instructions from the control board 224 and to turn on or off light emitted by the light sources 208. Alternatively, the control board 224 may control the electrical power provided to the light sources 208 so that the light sources 208 are turned on or off.

The camera 204 includes a lens 218 to focus light onto the photodetector 216. In some embodiments the lens 218 is a zoom lens that provides variable heightened image resolution. The zoom lens may be motorized and controlled by associated control circuitry (e.g., included in the control circuitry 214) or may be manually adjustable. The high resolution provided by a zoom lens enables accurate measurement of imaged skin features (e.g., pore size, hair strands, hair follicles, spots, and moles).

A polarizer 220 is mounted on the lens 218 and thereby coupled to the photodetector 216. In some embodiments, the polarizer 220 is an elliptical polarizer, or a circular polarizer, or a linear polarizer. In some embodiments, the polarizer 220 is rotatably mounted on the lens 218 so that the axis of the polarizer 220 can be rotated. Rotating the polarizer 220 provides an adjustable axis of polarization of light received by the photodetector 216. In some embodiments, a motor 222 attached to the polarizer 220 rotates the polarizer 220 (e.g., in defined angular increments) in response to instructions from polarizer control circuitry on a control board 224 coupled to the motor 222 via one or more signal lines 238. In some embodiments, the control board 224 or equivalent control circuitry is integrated into the motor 222 or camera control circuitry 214. Alternatively, a knob (not shown), if provided on the polarizer 220, allows manual adjustment of a degree of rotation of the polarizer 220.

The polarizer 220 may be adjusted such that it is aligned with the polarization of light emitted by the light sources 208 thereby admitting light of the same polarization as light emitted by the light sources 208 (e.g., specularly reflected light) while rejecting light of polarization perpendicular to the polarization of light from the sources 208. In this configuration, the polarizer 220 is parallel to the polarization of light emitted by the light sources 208. With the polarizer 220 in this configuration, the photodetector 216 may acquire an image of the subject 202 corresponding to light reflected from the surface of the subject's skin 203. An image of the subject 202 acquired while the polarizer 220 is parallel to the polarization of light emitted by the light sources 208 is called herein a parallel-polarization image.

The polarizer 220 may be adjusted such that it is perpendicular to, the polarization of light emitted by the light sources 208. In this configuration, the polarizer 220 rejects light of the same polarization as light emitted by the light sources 208 and admits light of polarization perpendicular to the light emitted by the light sources 208. With the polarizer 220 in this configuration, the photodetector 216 may acquire a sub-surface skin image of the subject 202 (e.g., corresponding to light reflected from a depth beneath the surface of the subject's skin 203 that varies from approximately 350 microns for very dark skin to approximately 3 mm for very fair skin). An image of the subject 202 acquired while the polarizer 220 is perpendicular to the polarization of light emitted by the light sources 208 is called herein a perpendicular-polarization image.

In some embodiments, the polarizer 220 is configured to rotate between 0° and 90° with respect to the polarization of light emitted by the light sources 208. In this configuration, the polarizer 220 admits partially polarized light. With the polarizer 220 in this configuration, the photodetector 216 may acquire an image of the subject 202 corresponding to a combination of surface and sub-surface skin images. This image may be processed to produce a sub-surface skin image by subtracting an image taken with 0° rotation of the polarizer 220. In some embodiments, the polarizer 220 is configured to rotate between 0° and 360° with respect to the polarization of light emitted by the light sources 208. Alternatively, the polarizer 220 is configured to rotate any angle with respect to the polarization of light emitted by the light sources 208.

In some embodiments, an imaging system includes a light shield 252 to shield the subject 202 from ambient light, as illustrated for the imaging system 250 (FIG. 2B) in accordance with some embodiments. In the system 250, the camera 204 is mounted on a back wall of the light shield 252. The camera 204 may extend outward from the camera housing 206 with a frusto-conical shape. By shielding the subject 202 from ambient light, the light shield ensures that most of the light reflected from the subject 202 is received at the photodetector 216.

In some embodiments, the system 250 includes a respective light source 208-5 that is distinct from the first light source 208-1 and the second light source 208-2. In some embodiments, the respective light source 208-5 is configured to emit light of a respective color that is distinct from the first color and the second color. In some embodiments, the respective light source 208-5 is configured to illuminate the subject 202 from the front of the subject. The respective light source 208-5 is typically coupled to the control board 224 (FIG. 2A) via one or more signal lines 210.

In some embodiments, the respective light source 208-5 is used for identifying surfaces that face the camera 204 (e.g., surfaces perpendicular to the direction from the surfaces to the camera 204). Due to the specular reflection, surfaces facing the camera 204 more strongly reflect light from the respective light source 208-5. The information about surfaces that face the camera 204 may be used for construction of normal maps. Normal maps are commonly used in 3D rendering to add details to a three-dimensional model without dramatically increasing the polygon count which can slow down the rendering process. For example, geometric details such as pores and wrinkles can be added to a coarse three-dimensional polygon model of a surface (e.g., a model generated based on information from stereo cameras). In addition, the normal maps may be used to correct errors where light occlusion has occurred (e.g., error caused by a shadow cast over a cheek by the nose may be corrected by using the normal maps).

A computer 226 (FIG. 2A) is coupled to the camera 204 and the control board 224 via one or more signal lines 236. The computer 226 includes memory 228 and one or more processors 230 as well as a monitor 232 for displaying a user interface (UI) 234. The UI 234 displays acquired and/or processed images as well as data calculated from acquired and/or processed images. In some embodiments, the computer 226 provides instructions to the control board 224 to rotate the polarizer 220, instructions to the camera 204 to adjust the zoom lens 218, and instructions to the camera 204 to acquire an image (i.e., to take a picture). The computer 400 (FIG. 4, below) illustrates an example of an implementation of the computer 226 in accordance with some embodiments.

In some embodiments, the functionality of the computer 226 and the control board 224 is integrated into the camera 204. In some embodiments, the camera 204 includes a display for viewing acquired and/or processed images as well as data calculated from acquired and/or processed images. In some embodiments, the control board 224 is included in the computer 226.

In some embodiments, the light sources 208 and camera 204 (including the polarizer 220) are mounted in an imaging box 302, as illustrated for the imaging system 300 (FIG. 2C). The imaging box 302 may include additional components that are not illustrated in FIG. 2C. The imaging box 302, shown as mounted on a cart 310 for mobility, serves as a light shield (e.g., light shield 252, FIG. 2B) to shield the subject from ambient light. Light sources 208-1 through 208-4 are mounted on a rear wall of the box 302, opposite from a chin rest 306 and forehead pad 304 for receiving the subject's head. The system 300 may include a printer 308 for printing acquired and/or processed images as well as data calculated from acquired and/or processed images.

In some embodiments, a reference material is included in acquired images to measure changes in the light source (e.g., intensity output change and/or color change over time, resulting from, for example, drift in a light source 208). For example, a standard color chart such as the GretagMacbeth ColorChecker is placed in the field of imaging (e.g., beneath the chin of the subject 202) and used to calibrate the photodetector 216 and/or to post-process acquired images to adjust pixel values based on comparison to known pixel values for colors in the color chart. Furthermore, image processing software may be used to correct for optical aberrations.

Figure 2B:
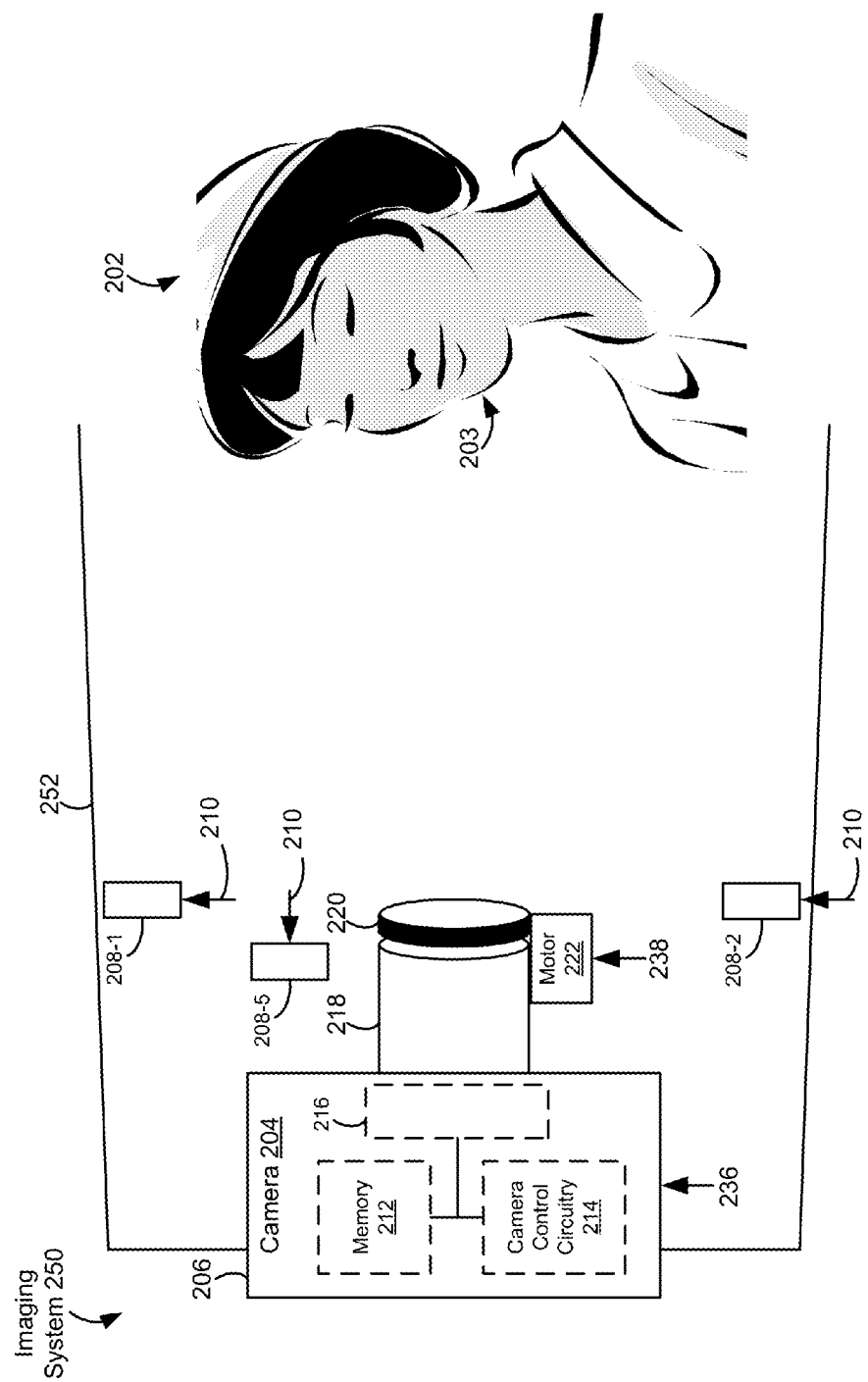
Figure 3A:
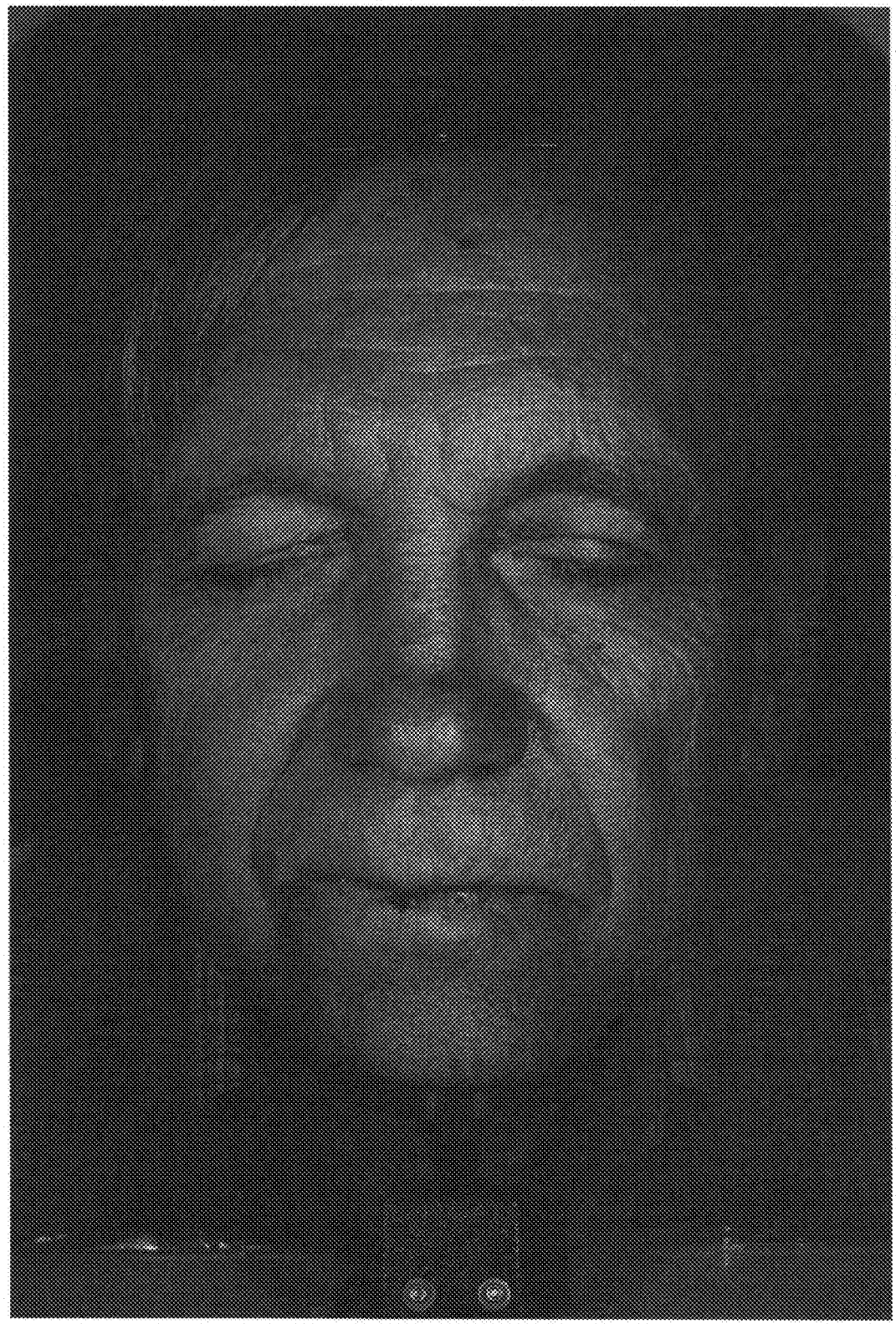
FIGS. 3A-3B are exemplary images of a subject illuminated with a plurality of light sources in accordance with some embodiments.
Figure 3B:
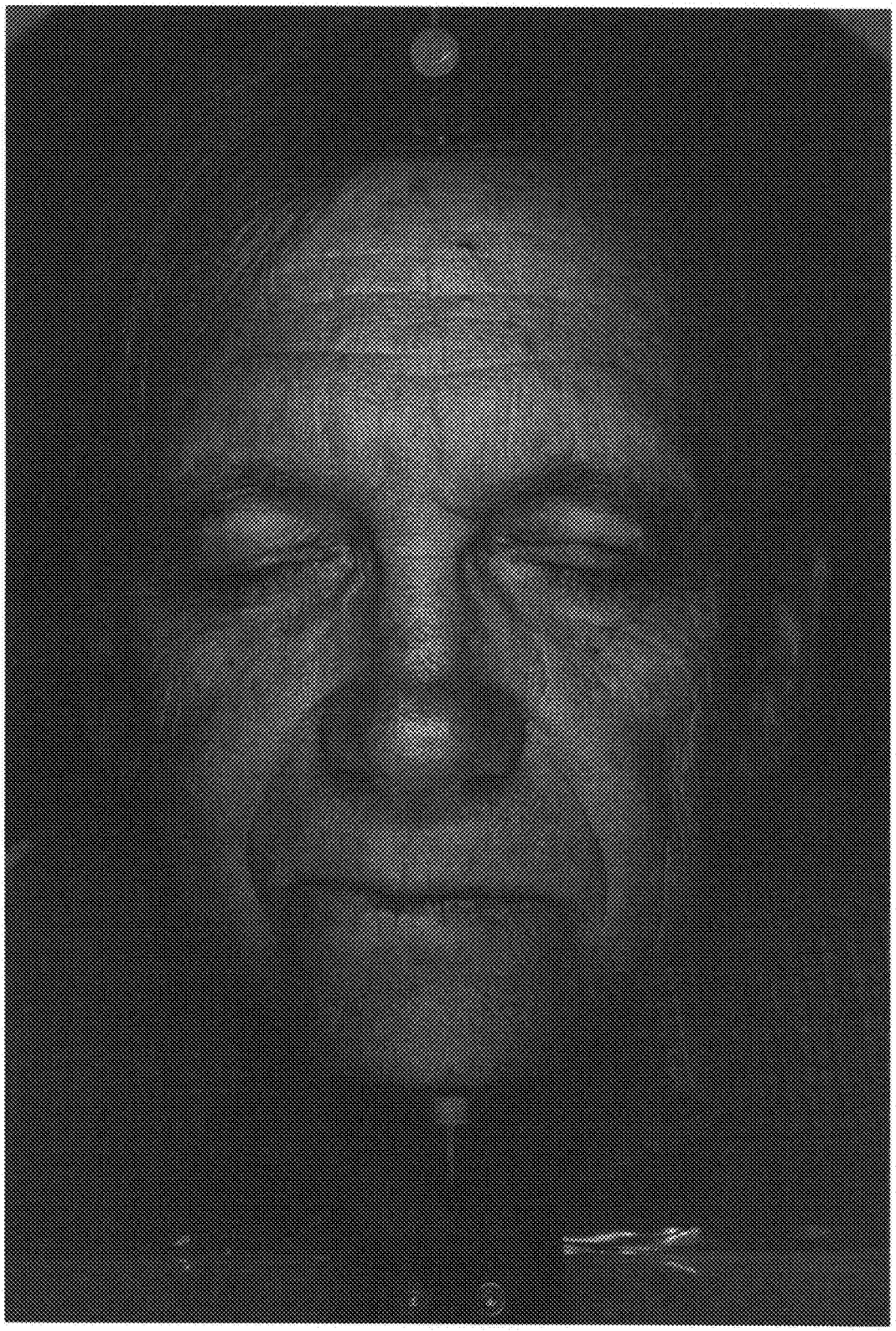

FIGS. 3A-3B are exemplary images of a subject illuminated with a plurality of light sources in accordance with some embodiments. The images in FIGS. 3A-3B may be acquired by an imaging system illustrated in FIGS. 2A-2C (e.g., the imaging system 200, 250, or 300).

The image in FIG. 3A is an image of the subject illuminated with two distinct light sources. For example, the subject in FIG. 3A is illuminated with blue light from the left side of the subject and green light from the right side of the subject. As used with respect to FIG. 3A, the "left side" refers to the left side of the subject as seen by a viewer facing the front of the subject. Similarly, as used in this paragraph, the "right side" refers to the right side of the subject as seen by the viewer facing the front of the subject. Such terms do not refer to the sides as perceived by the subject. However, it should be noted that the location of each light source may be interchanged. For example, blue light may be used to illuminate the right side of the subject and green light may be used to illuminate the left side of the subject. Alternatively, any other combination of two distinct colors may be used to illuminate the left side and the right side of the subject.

The image in FIG. 3B is an image of the subject illuminated with two distinct light sources. For example, the subject in FIG. 3B is illuminated with blue light from a lower side of the subject and green light from an upper side of the subject. As explained above, green light may be used to illuminate from the lower side of the subject and blue light may be used to illuminate the upper side of the subject. Alternatively, any other combination of two distinct colors may be used to illuminate the subject from the upper side of the subject and the lower side of the subject, respectively.

In FIGS. 3A-3B, a region of the subject that is closer to a particular light source reflects more intensely light of a color that corresponds to the particular light source. Thus, in FIG. 3A, the left side of the subject is dominantly illuminated with blue light. However, it should be noted that each light source illuminates an entire surface of the subject that is to be profiled. For example, the left side of the subject is also illuminated with green light. Similarly, the right side of the subject is also illuminated with blue light.

From the image acquired while illuminating the subject from the left side and the right side, respective intensity values corresponding to respective colors are extracted and used to determine a horizontal tilt $\alpha$ (e.g., whether the surface faces toward the left side or the right side). Similarly, from the image acquired while illuminating the subject from the upper side and the lower side, respective intensity values corresponding to respective colors are extracted and used to determine a vertical tile $\beta$ (e.g., whether the surface faces toward the upper side or the lower side).

In some embodiments, a single four-color image of the subject is acquired and used, instead of two two-color images, for determining the surface profile. For example, when the subject is concurrently illuminated with blue, green, red, and yellow light, respective values corresponding to the respective intensities of light of respective colors (e.g., a first value representing an intensity of blue light, a second value representing an intensity of green light, a third value representing an intensity of red light, and a fourth value representing an intensity of yellow light) may be extracted from the four-color image, and used to determine the horizontal tilt $\alpha$ and the vertical tilt $\beta$.

As used herein, a two-color image refers to an image obtained while the subject is illuminated concurrently with light sources of two distinct colors, and a four-color image refers to an image obtained while the subject is illuminated concurrently with light sources of four distinct colors. However, it should be noted that the two-color image may include more than two colors, and the four-color image may include more than four colors.

Figure 3C:
FIG. 3C is a grayscale image of the subject in accordance with some embodiments.

FIG. 3C is an exemplary grayscale image of the subject in accordance with some embodiments. Grayscale intensity values in FIG. 3C are generated from the color image shown in FIG. 3A. FIG. 3C shows an area on the subject (indicated with a white square) corresponding an exemplary surface profile 350 of the subject shown in FIG. 3D.

Figure 3D:
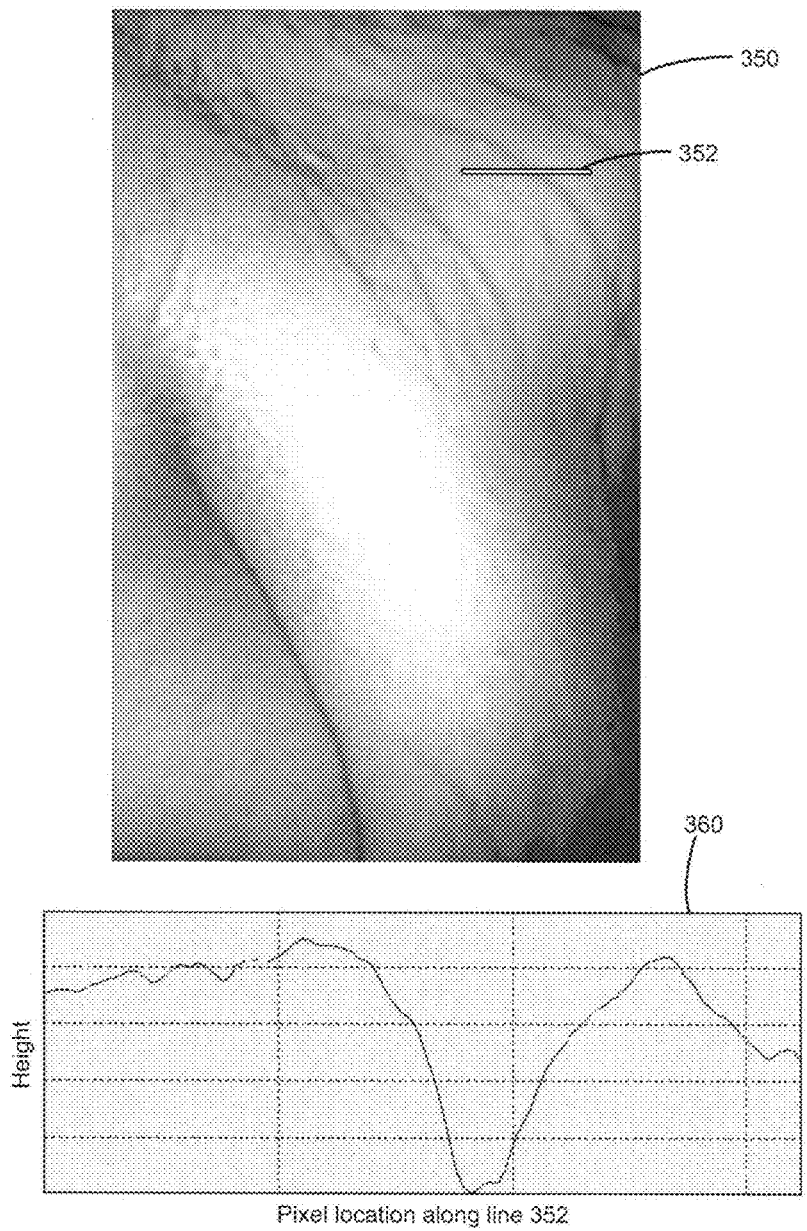
FIG. 3D illustrates an exemplary surface profile showing one or more wrinkles of the subject in accordance with some embodiments.

FIG. 3D shows the exemplary surface profile 350 of the subject in accordance with some embodiments. The surface profile 350 shown in FIG. 3D is generated based on the images illustrated in FIGS. 3A and 3B.

In FIG. 3D, the intensity value at each region (e.g., a pixel) corresponds to a height (or displacement) of the region. A height profile 360 in FIG. 3D shows the variation in height of the surface corresponding to a line 352 shown over the surface profile 350. In particular, the height profile 360 corresponds to a cross-section of a wrinkle. Thus, from the height profile 360, the depth and width of the wrinkle can be determined. Similarly, a length of a wrinkle can be determined from a height profile along the wrinkle.

Figure 3E:
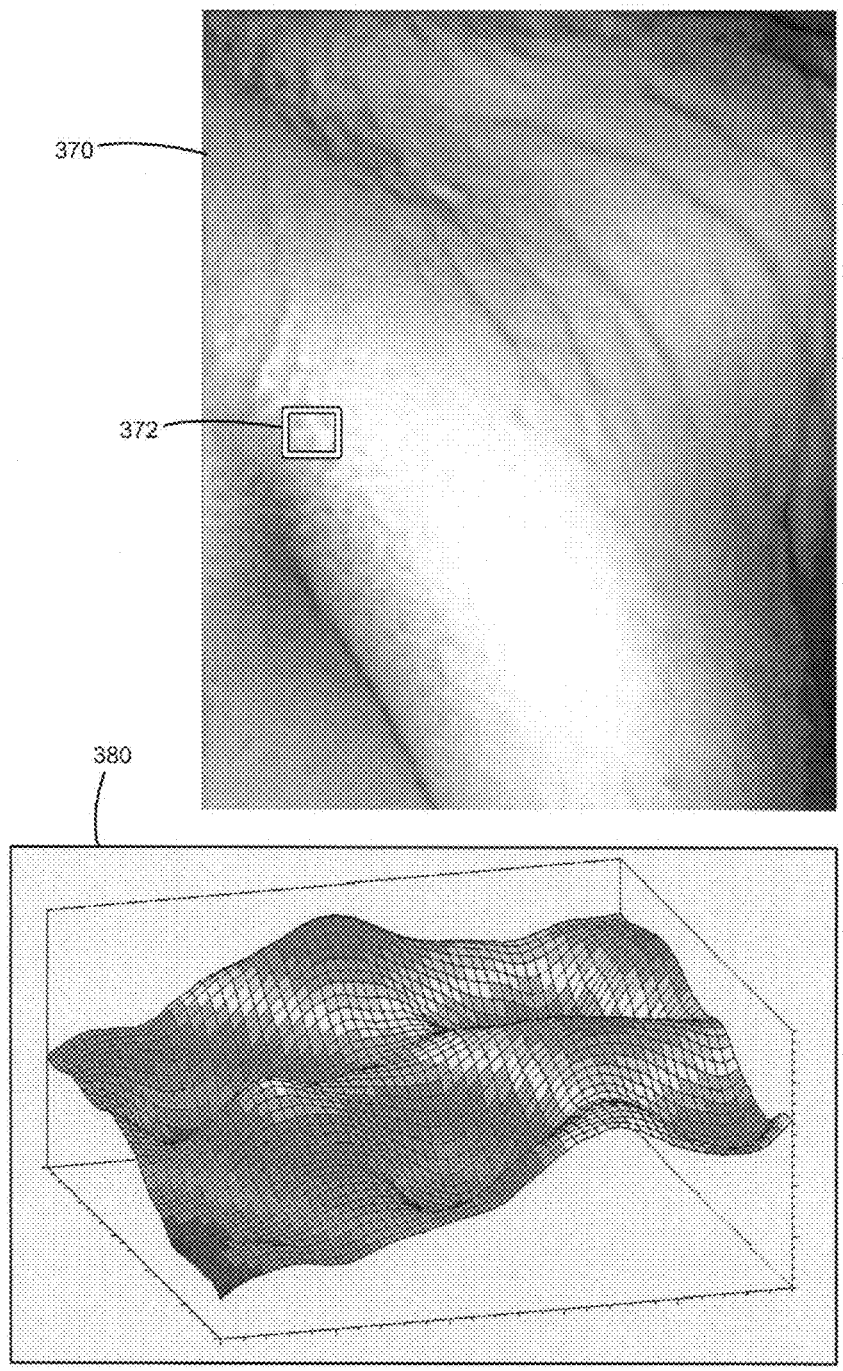
FIG. 3E illustrates an exemplary surface profile showing pores of the subject in accordance with some embodiments.

FIG. 3E illustrates an exemplary surface profile 370 in accordance with some embodiments. The exemplary surface profile 370 corresponds to a portion of the surface profile 360 shown in FIG. 3D. Shown over the surface profile 370 is a marker 372 that indicates an area for which a three-dimensional surface profile 380 is shown. The three-dimensional surface profile 380 is a three-dimensional view of a portion of the surface profile 370 that corresponds to the location of the marker 372. The three-dimensional surface profile 380 shows at least three pores located within the area corresponding to the marker 372. From the three-dimensional surface profile 380, the number of pores within the area may be determined. In addition, the size (e.g., width and/or depth) of one or more pores may be determined from the three-dimensional surface profile 380.

Figure 4:
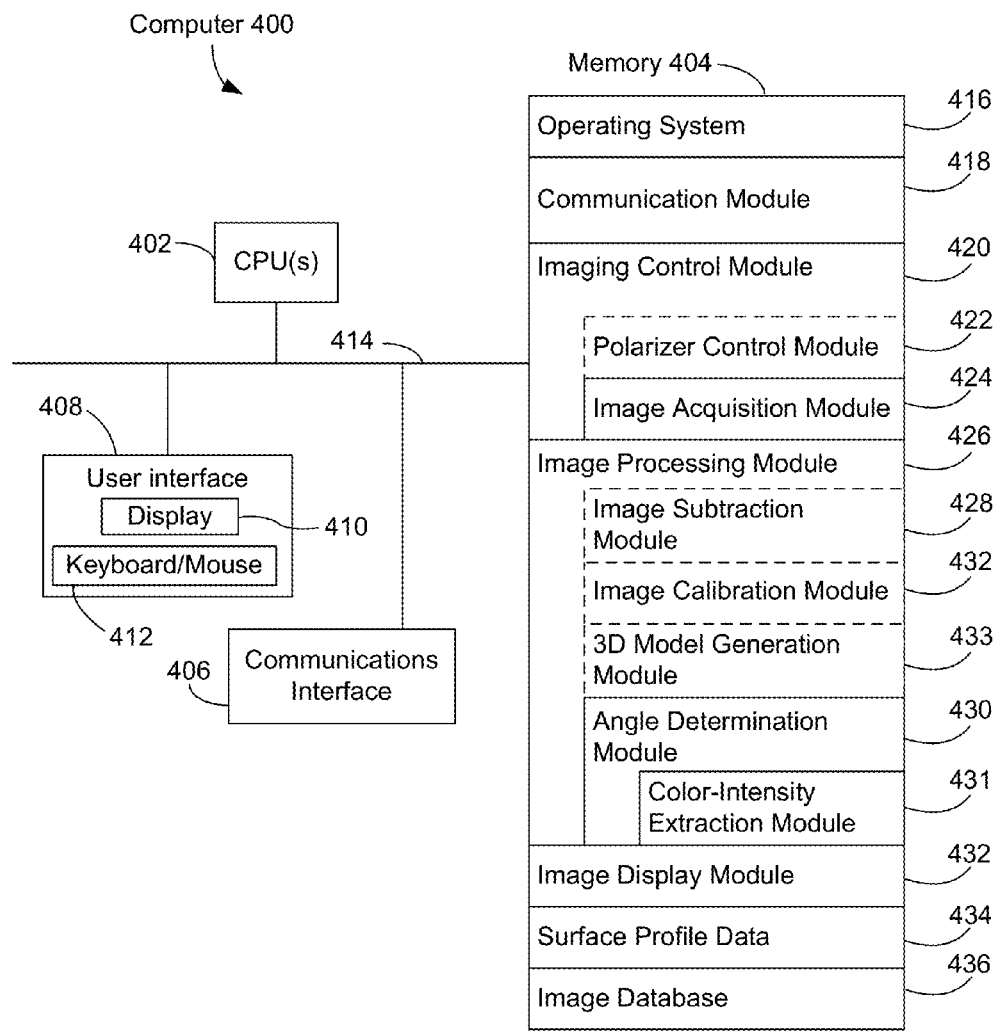
FIG. 4 is a block diagram illustrating a computer system configured for use with the imaging system in accordance with some embodiments.
Figure 6B:
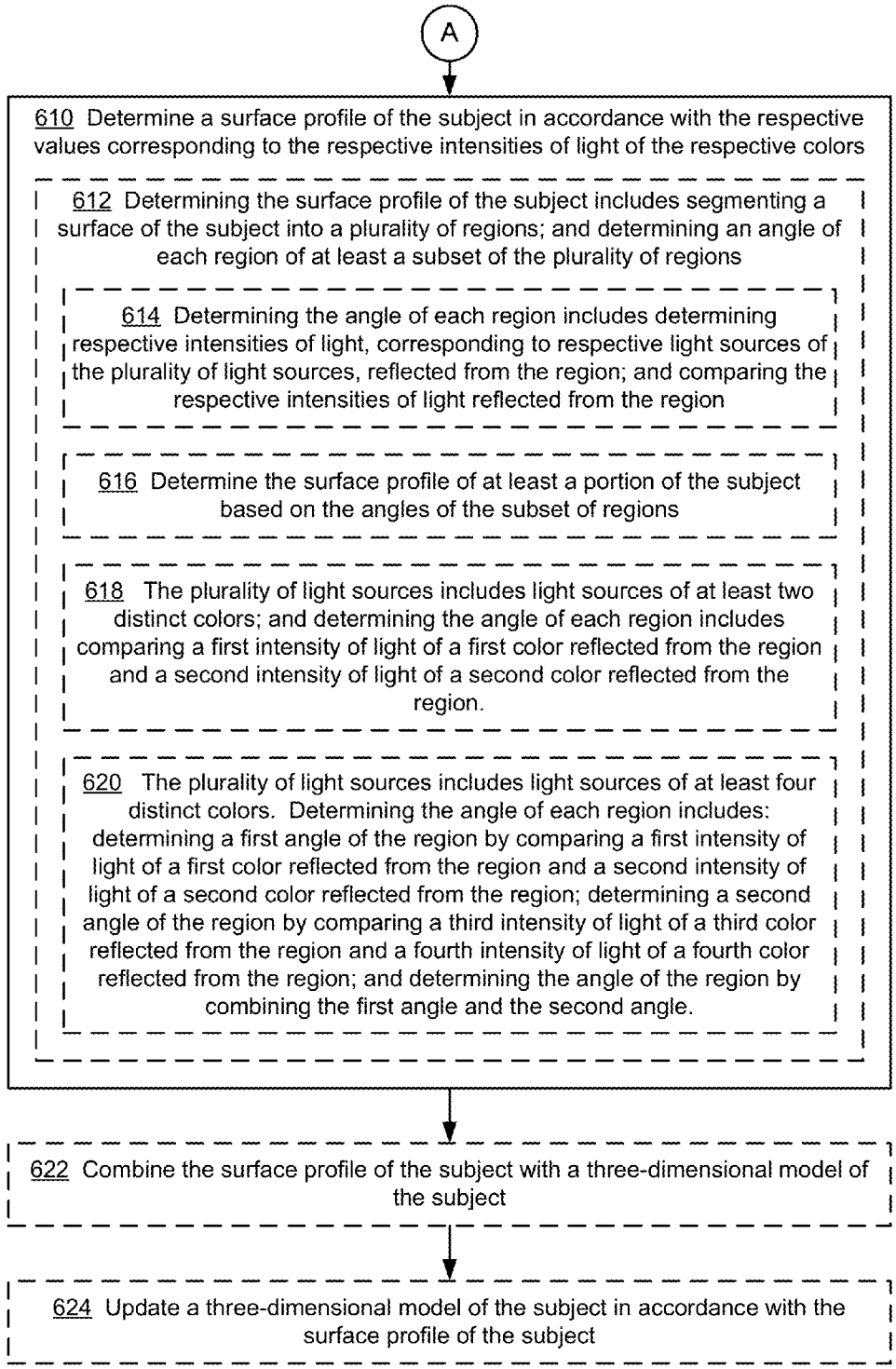

FIG. 4 is a block diagram illustrating a computer system 400 in accordance with some embodiments. In some embodiments the computer 400 is an example of an implementation of the computer 226 (FIGS. 2A and 2C). The computer 400 typically includes one or more central processing units (CPUs) 402, one or more communications interfaces 406, memory 404, and one or more communication buses 414 for interconnecting these components. The communication buses 414 may include circuitry (sometimes called a chipset) that interconnects and controls communications between system components. The computer 400 may also include user interface hardware 408 comprising a display device 410 (e.g., the monitor 232, FIG. 2A) and a keyboard and/or mouse (or other pointing device) 412. The memory 404 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. The memory 404 may optionally include one or more storage devices remotely located from the CPU(s) 402. The memory 404, or alternately non-volatile memory device(s) within the memory 404, comprises a non-transitory computer readable storage medium. In some embodiments, the memory 404 stores instructions for performing all or a portion of the method 600 (FIGS. 6A-6B). In some embodiments, the memory 404 stores the following programs, modules, and data structures, or a subset thereof:

- an operating system 416 that includes procedures for handling various basic system services and for performing hardware dependent tasks;
- a communication module 418 that is used for connecting the computer 400 to one or more cameras (e.g., the camera 204, FIG. 2A) and/or other computers via the one or more communications interfaces 406;
- an imaging control module 420 for controlling an imaging system (e.g., the system 200, 250, and 300, FIGS. 2A-2C);
- an image processing module 426 to process acquired images (e.g., images acquired using the system 200, 250, and 300, FIGS. 2A-2C);
- an image display module 432 module to display skin images and data corresponding to skin images;
- surface profile data 434; and
- image database 436.

Figure 5:
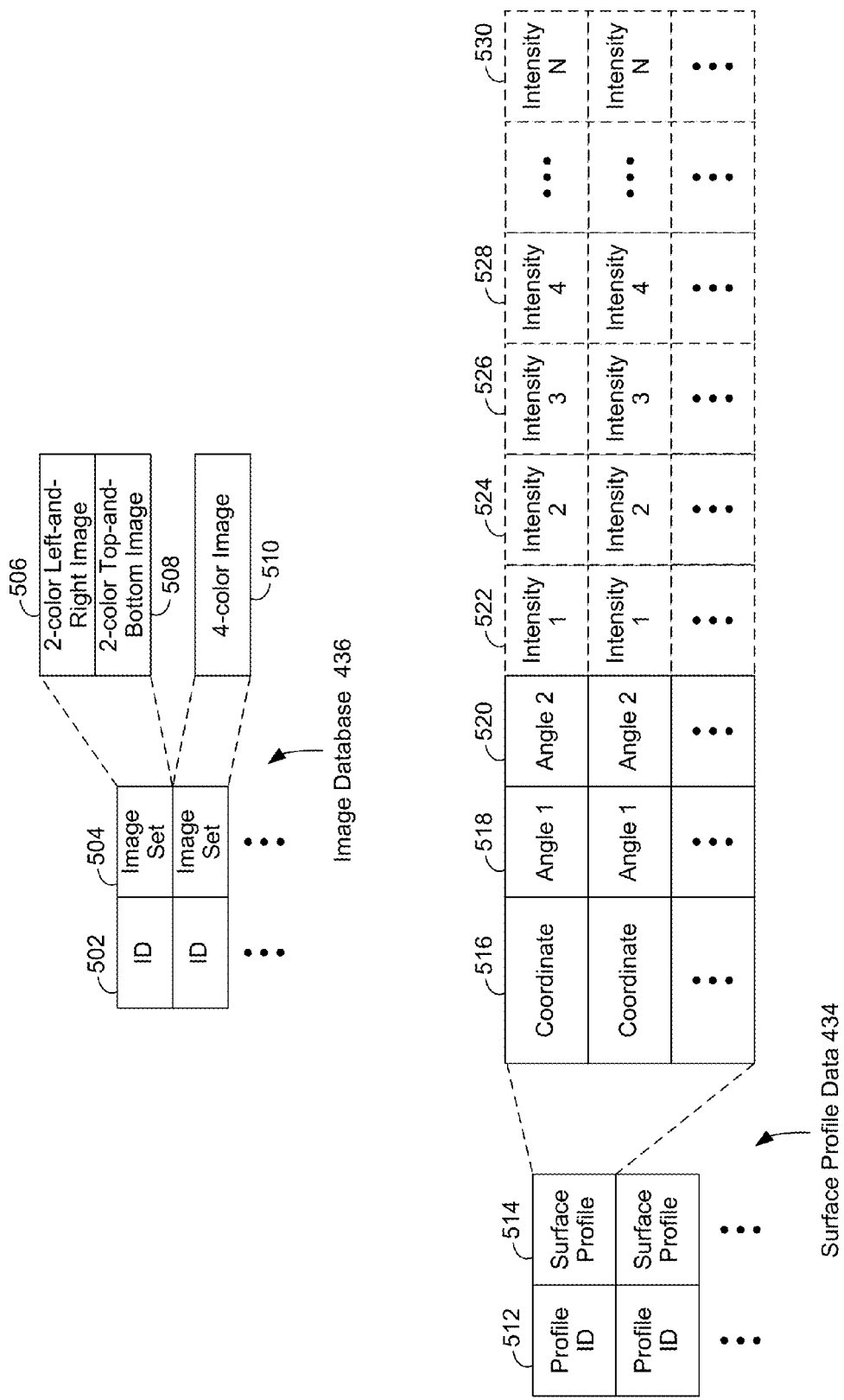
FIG. 5 is a block diagram illustrating exemplary data structures in accordance with some embodiments.

The surface profile data 434 and the image database 436 are described in detail with respect to FIG. 5.

In some embodiments, the imaging control module 420 includes a polarizer control module 422 for automatically controlling an adjustable polarizer (e.g., for controlling the motor 222 via the control board 224, FIG. 2A) and/or an image acquisition module 424 for controlling image acquisition (e.g., with the camera 204, FIGS. 2A-2C).

The image processing module 426 includes an angle determination module 430, which is configured to determine an orientation (or angle) for respective regions of a surface based on one or more acquired images. The angle determination module 430 includes a color-intensity extraction module 431 for extracting intensity of predefined color corresponding to the respective regions of the surface from the one or more acquired images.

In some embodiments, the image processing module 426 also includes one or more of: an image subtraction module 428 for subtracting respective acquired images, an image calibration module 432, and a three-dimensional model generation module 433 (e.g., for generating a three-dimensional model of a subject).

Each of the above identified elements in FIG. 4 may be stored in one or more of the previously mentioned memory devices. Each of the above-identified modules corresponds to a set of instructions for performing a function described above. These sets of instructions need not be implemented as separate software programs, procedures or modules. Various subsets of the above-identified modules may be combined or otherwise re-arranged in various embodiments. In some embodiments, the memory 404 may store a subset of the modules and data structures identified above. Furthermore, the memory 404 may store additional modules and data structures not described above.

FIG. 5 is a block diagram illustrating exemplary data structures in accordance with some embodiments.

The image database 436 typically includes a plurality of entries. Each entry in the image database 436 includes an identifier (ID) 502 and at least one image set 504. The identifier 502 uniquely identifies each subject and/or each image set of a respective subject. In some cases, multiple image sets may correspond to a single subject (e.g., a first image set is acquired at a first time, and a second image set is acquired at a second time). A respective image set 504 may include two or more two-color images or one or more four-color images. Each two-color image comprises an image of the respective subject concurrently illuminated with light of two different colors (e.g., red and green, yellow and blue, or a pair of any two distinct colors). Each four-color image comprises an image of the respective subject concurrently illuminated with light of four different colors (e.g., red, green, yellow, and blue).

In some embodiments, when the respective image set 504 includes two or more two-color images, the two-color images include: at least one image of the subject illuminated with light of a first color from a first direction (e.g., left) and light of a second color from a second direction (e.g., right), and at least one image of the subject illuminated with light of a third color from a third direction (e.g., top) and light of a fourth color from a fourth direction (e.g., bottom). The first color is distinct from the second color, and the third color is distinct from the fourth color. However, the first color need not be distinct from the third or fourth color, and the second color need not be distinct from the third or fourth color. For example, a first two-color image in a respective set may be an image of the subject illuminated with light of the first color from the first direction and light of the second color from the second direction, and a second two-color image in the respective set may be an image of the subject illuminated with light of the first color from the third direction (distinct from the first direction) and light of the second color from the fourth direction (distinct from the second direction).

In some embodiments, when the respective image set 504 includes a four-color image, the four-color image comprises an image of the subject illuminated with light of a first color from a first direction (e.g., left), light of a second color from a second direction (e.g., right), light of a third color from a third direction (e.g., top), and light of a fourth color from a fourth direction (e.g., bottom). The first, second, third, and fourth colors are all distinct colors.

In some embodiments, the respective image set 504 includes an N-color image, where N is a number of colors used concurrently to illuminate the subject. The number N may be larger than four (e.g., five or more).

FIG. 5 also includes the surface profile data 434, which includes one or more entries. Each entry in the surface profile data 434 includes a profile identifier 512 and a surface profile 514. The surface profile 514 includes a plurality of entries, each corresponding to a respective region of a surface of the respective subject. Each entry in the surface profile 514 includes a coordinate 516 that uniquely identifies the respective region (or location) of the surface of the respective subject. For example, the coordinate 516 may be an x and y coordinate or a pixel number that uniquely identifies a corresponding pixel in an acquired image. Each entry in the surface profile 514 also includes one or more angles (e.g., an angle 518 and an angle 520) that are used to determine a surface normal of the respective region of the surface.

In some embodiments, each entry in the surface profile 514 also includes an intensity corresponding to each color. For example, when the image set 504 includes a four-color image (e.g., the image 510), an entry in the surface profile 514 corresponding to the four-color image includes an intensity 522 of light of a first color (e.g., red) reflected from the respective region of the surface, an intensity 524 of light of a second color (e.g., green) reflected from the respective region of the surface, an intensity 526 of light of a third color (e.g., yellow) reflected from the respective region of the surface, and an intensity 528 of light of a fourth color (e.g., blue) reflected from the respective region of the surface. When the image set 504 includes two two-color images, an entry in the surface profile 514 corresponding to the two-color images may include an intensity 522 of a first color (e.g., red) reflected from the respective region of the surface in a first two-color image (e.g., an image with left-and-right illumination), an intensity 524 of a second color (e.g., green) reflected from the respective region of the surface in the first two-color image, intensity 526 of the first color (e.g., red) reflected at a corresponding region of the surface in a second two-color image (e.g., an image with top-and-bottom illumination), and intensity 528 of the second color (e.g., green) reflected from the corresponding region of the surface in the second two-color image. In some embodiments, each entry in the surface profile 514 may include intensity 530 of an N-th color.

FIGS. 6A-6B are flow diagrams illustrating a method 600 of determining a surface profile of skin in accordance with some embodiments. The method is performed at an imaging system (e.g., the imaging system 200, 250, and 300, FIGS. 2A-2C).

The system illuminates (602) a subject with light from a plurality of light sources. The plurality of light sources has distinct colors and configured to illuminate the subject from distinct locations. For example, each light source has a distinct color (e.g., one of: blue, green, yellow, and red) and is located at a distinct location (e.g., 208-1 through 208-4, FIG. 2C).

In some embodiments, the plurality of light sources emits (604) light of respective colors that have distinct spectra. In some embodiments, a first light source emits light within a first wavelength range, a second light source emits light within a second wavelength range, and the first wavelength range and the second wavelength range do not overlap. For example, the first light source may emit light of a wavelength within a 630-650 nm range, and the second light source may emit light of a wavelength within a 550-570 nm range. Alternatively, the plurality of light sources emits light that have spectrally resolvable spectra. For example, although the light emitted by the first light source and the light emitted by the second light source may at least partially overlap, a first spectrum of the light emitted by the first light source and a second spectrum of the light emitted by the second light source are distinct such that they can be spectrally resolved.

The system obtains (606) a multi-color image of the subject. The multi-color image comprises respective values corresponding to respective intensities of light of respective colors for each region of the subject. In some embodiments, the multi-color image includes respective values corresponding to respective intensities of light of respective colors reflected from each region of the subject. For example, the respective values corresponding to the respective intensities of light of respective colors may range from 0 to 255, where the value 0 represents the lowest intensity and the value 255 represents the highest intensity. In some embodiments, the multi-color image includes separately the respective values corresponding to respective intensities of light of respective colors for each region of the subject. For example, an RGB image includes separately intensity values for red, green, and blue components of light for each pixel. In some embodiments, values corresponding to intensities of light of certain colors are calculated from the values corresponding to other colors. For example, in an RGB image that does not separately includes an intensity value for yellow color, the value corresponding to the yellow color are calculated from other values stored in the RGB image.

In some embodiments, the system first illuminates the subject using a first light source of a first color and a second light source of a second color distinct from the first color. The first light source is configured to illuminate the subject from a first location, and the second light source is configured to illuminate the subject from a second location distinct from the first location. The system obtains a first two-color image of the subject while the subject is concurrently illuminated using the first light source and the second light source. The system then illuminates the subject using a third light source of a third color and a fourth light source of a fourth color distinct from the third color. The third light source is configured to illuminate the subject from a third location distinct from the first and second locations, and the fourth light source is configured to illuminate the subject form a fourth location distinct from the first, second, and third locations. The system obtains a second two-color image of the subject while the subject is concurrently illuminated using the third light source and the fourth light source.

In some embodiments, the system concurrently illuminates the subject using the first light source of the first color, the second light source of the second color, the third light source of the third color, and the fourth light source of the fourth color. The first light source is configured to illuminate the subject from the first location, and the second light source is configured to illuminate the subject from the second location distinct from the first location. The third light source is configured to illuminate the subject from the third location distinct from the first and second locations, and the fourth light source is configured to illuminate the subject form the fourth location distinct from the first, second, and third locations. The system obtains a four-color image of the subject while the subject is concurrently illuminated using the first light source, the second light source, the third light source, and the fourth light source.

The specularly reflected light reflected off the surface of the subject is useful in determining a surface profile of the subject. Therefore, in some embodiments, the system acquires a parallel-polarization image while an axis of the polarizer 220 (FIG. 2A) is aligned with the polarization of light impinging on the subject 202.

However, the parallel-polarization image may still include a small contribution from diffusely reflected light, and in some cases, it is advantageous to remove the contribution from diffusely reflected light. Thus, in some embodiments, obtaining the multi-color image includes (608): obtaining a parallel-polarization image of the subject; obtaining a cross-polarization image of the subject; and subtracting the cross-polarization image of the subject from the parallel-polarization image of the subject to produce the multi-color image of the subject. For example, the parallel-polarization image is obtained by taking an image with the imaging system 200 (FIG. 2A) while an axis of the polarizer 220 is aligned with a polarization of the light impinging on the subject 202, and the cross-polarization image of the subject is obtained by taking an image while the axis of the polarizer 220 is perpendicular to the polarization of the light impinging on the subject 202. Subtracting the cross-polarization image of the subject from the parallel-polarization image of the subject further reduces the contribution from diffusely reflected light, and maintains the contribution from specularly reflected light. Thus, in some embodiments, only the contributions from specularly reflected light are obtained by subtracting the cross-polarization image of the subject from the parallel-polarization image of the subject. In some embodiments, intensity normalization is performed prior to subtracting the cross-polarization image of the subject from the parallel-polarization image of the subject. For example, the intensity in the cross-polarization image of the subject is scaled to match the intensity of diffusely reflected light in the parallel-polarization image.

In some embodiments, the system normalizes the respective values corresponding to the respective intensities of light of the respective colors. For example, the normalization may be achieved through the use of color charts or color checkers that are typically used to white balance photographic images. These color checkers are typically within the field of view of the images being captured. A monochrome reference surface is typically used to measure the relative intensity of light of two or more colors (e.g., light emitted by green and blue LED devices). If light of one color is found to be brighter than light of the other color, their brightness is computationally adjusted in the image so that their intensities are matched on this monochrome reference. In other words, when a first value corresponding to a first intensity of light of a first color on the reference surface does not match a second value corresponding to a second intensity of light of a second color on the reference, a normalization factor is determined. In some embodiments, the normalization factor is a ratio of the first value corresponding to the first intensity of light of the first color and the second value corresponding to the second intensity of light of the second color. The normalization factor may be used to adjust the intensity values of one or more colors in the multi-color image of the subject. This normalization operation may be performed before the surface profile is determined.

The normalization operation is important, when the first value corresponding to the first intensity of light of the first color on the reference surface does not match the second value corresponding to the second intensity of light of the second color on the reference surface, because the ratio of the intensities of light of the first and second colors on a respective region determines the angle of the respective region. For example, when a first light source produces light of higher intensity compared to a second light source, the surface profile of the subject may be erroneously skewed (or tilted) without the normalization operation.

The system determines (610) a surface profile of the subject in accordance with the respective values corresponding to the respective intensities of light of the respective colors. Because the intensity of each color at each location depends on the surface profile of the subject, the surface profile of the subject can be determined from the intensity of each color at each location.

In some embodiments, determining the surface profile of the subject includes (612): segmenting a surface of the subject into a plurality of regions; and determining an angle of each region of at least a subset of the plurality of regions. For example, the image is segmented into a plurality of pixels or super-pixels, and the respective angle of respective pixels or super-pixels is determined. In turn, the surface profile may be created from the respective angle of the respective regions, for example, by using a three-dimensional surface reconstruction algorithm (e.g., Frankot-Chellappa algorithm).

In some embodiments, determining the angle of each region includes (614): determining respective intensities of light, corresponding to respective light sources of the plurality of light sources, reflected from the region; and comparing the respective intensities of light reflected from the region. For example, when a four-color image is obtained for the subject, four intensity values, each corresponding to each color, are obtained for each region (e.g., pixel). When two two-color images are obtained for the subject, first and second intensity values are obtained for each region in the first two-color image, and third and fourth intensity values are obtained for corresponding regions in the second two-color image. In some embodiments, the ratio of the first and second intensity values determines a first angle indicating a tilt of the surface along a first axis (e.g., a horizontal axis), and the ratio of the third and fourth intensity values determines a second angle indicating a tile of the surface along a second axis (e.g., a vertical axis).

In some embodiments, the system determines (616) the surface profile of at least a region of the subject based on the angles of the subset of regions. For example, the system may integrate the angle of each region to determine the displacement (or height) of the respective region. In some embodiments, the displacement (or height) of the respective region is determined in accordance with the equation 1 described above with respect to FIG. 1E. Alternatively, the displacement (or height) of the respective region is determined based on a finite element model corresponding to the angles (or orientations) of the respective regions.

In some embodiments, the plurality of light sources includes (618) light sources of at least two distinct colors. Determining the angle of each region includes comparing a first intensity of light of a first color reflected from the region and a second intensity of light of a second color reflected from the region.

In some embodiments, the plurality of light sources includes (620) light sources of at least four distinct colors. Determining the angle of each region includes: determining a first angle of the region by comparing a first intensity of light of a first color reflected from the region and a second intensity of light of a second color reflected from the region; determining a second angle of the region by comparing a third intensity of light of a third color reflected from the region and a fourth intensity of light of a fourth color reflected from the region; and determining the angle of the region by combining the first angle and the second angle. For example, based on the respective values corresponding to the respective intensities of light of two colors (e.g., red and green), an angle $\alpha$ between a projection 170 of the surface normal (e.g., on a plane formed by the predefined axes 156 and 158) and a first predefined axis 154 is determined (e.g., FIG. 1G). Similarly, based on the respective values corresponding to the respective intensities of light of two colors (e.g., blue and yellow), an angle $\beta$ between a projection 172 of the surface normal (e.g., on a plane formed by the predefined axes 154 and 158) and a second predefined axis 156 is determined (e.g., FIG. 1G). In some embodiments, other angles are determined based on the angles $\alpha$ and $\beta$. For example, the angles between the surface normal and two predefined axes (e.g., $\theta_1$ and $\theta_2$, FIG. 1F) may be determined from the angles $\alpha$ and $\beta$.

In some embodiments, the angle $\alpha$ of a respective region along the first predefined axis is determined in accordance with the following equation:

$$A_1 = I_1/(I_1+I_2) \quad \text{(Eq. 2)}$$

where $A_1$ is a value corresponding to the angle $\beta$ of the respective region along the first predefined axis, $I_1$ is the first intensity of light of the first color reflected from the region, and $I_2$ is the second intensity of light of the second color reflected from the region.

Similarly, the angle $\beta$ of the respective region along the second predefined axis may be determined in accordance with the following equation:

$$A_2 = I_3/(I_3+I_4) \quad \text{(Eq. 3)}$$

where $A_2$ is a value corresponding to the angle $\beta$ of the respective region along the second predefined axis, $I_3$ is the third intensity of light of the third color reflected from the region, and $I_4$ is the fourth intensity of light of the fourth color reflected from the region.

When both $A_1$ and $A_2$ have a value of 0.5, the respective region is deemed to be perfectly normal to the direction from the camera (e.g., flat when viewed from the camera). When either $A_1$ or $A_2$ has a value of 0 or 1, the respective region is facing 90 degrees away from the camera.

In some embodiments, the respective intensity values (e.g., $I_1$, $I_2$, $I_3$, and $I_4$) correspond to a difference between respective intensity values of specularly reflected light of respective colors and respective intensity values of diffusely reflected light of respective colors.

In some embodiments, the plurality of light sources includes a first light source of a first color, a second light source of a second color, a third light source of the third color, and a fourth light source of the fourth color. The first light source and the second light source are located along the first predefined axis, and the third light source and the fourth light source are located along the second predefined axis. In some embodiments, the system obtains a first multi-color image of the subject illuminated with the first light source and the second light source, and a second multi-color image of the subject illuminated with the third light source and the fourth light source. Determining the angle of each region includes determining, for the region, a first angle (e.g., angle $\alpha$) along the first predefined axis and a second angle (e.g., angle $\beta$) along the second predefined axis. Determining the first angle includes comparing a first intensity of light of the first color, emitted from the first light source and reflected from the region, and a second intensity of light of the second color, emitted from the second light source and reflected from the region (e.g., the blue and green light in the image shown in FIG. 3A). Determining the second angle includes comparing a third intensity of light of the third color, emitted from the third light source and reflected from the region, and a fourth intensity of light of the fourth color, emitted from the fourth light source and reflected from the region (e.g., the blue and green light in the image shown in FIG. 3B). In some embodiments, the first color corresponds to the third color (e.g., the first color and the third color are a same color), and the second color corresponds to the fourth color (e.g., the second color and the fourth color are a same color).

In some embodiments, the system combines (622) the surface profile of the subject with a three-dimensional model of the subject. For example, three-dimensional models of subjects (e.g., a wireframe model of the subject) often do not include information about features of a size smaller than a wire mesh used in the wireframe model. By combining the surface profile of the subject with a three-dimensional model, the three-dimensional model can be used for analyses that require information about detailed features (e.g., wrinkle characteristics, skin aging, etc.).

In some embodiments, the system updates (624) a three-dimensional model of the subject in accordance with the surface profile of the subject. For example, a surface profile of the subject may be extracted from the three-dimensional model and compared with the surface profile of the subject determined using the plurality of light sources. The surface profile of the subject determined using the plurality of light sources may be used to adjust the three-dimensional model of the subject so that the extracted surface profile matches the surface profile determined using the plurality of light sources.

In some embodiments, a three-dimensional model of a subject is generated by the computer 226 performing a process of morphing a generic face based on the acquired images that includes generating a distance map from points in the images of the subject to image features, as described for example in C. Zhang et al., "3-D Face Structure Extraction and Recognition from Images using 3-D Morphing and Distance Mapping," IEEE Transactions on Image Processing, Vol. 11, No. 11, pp. 1249-59 (November 2002), which is hereby incorporated by reference herein in its entirety. In another example, a morphing process is used as described in V. Blanz et al., "A Morphable Model for the Synthesis of 3D Faces," SIGGRAPH 99, pp. 187-194 (1999), which is hereby incorporated by reference herein in its entirety. In some embodiments, the morphing and distance mapping process is enhanced by using structured light projected onto the subject. For example, the subject is illuminated through a patterned substrate, which results in the projection of structured light (e.g., a light grid or array of points of light) onto the subject. The structured light is used to identify points on the subject (e.g., on the subject's face) in the distance-mapping and morphing process, as described in U.S. patent application Ser. No. 13/078,834, filed Apr. 1, 2011, entitled "Methods and Systems for Imaging and Modeling Skin Using Polarized Lighting," which is incorporated by reference herein in its entirety.

In some embodiments, the surface profile is analyzed for feature measurements, including pore size measurements, wrinkle length and depth measurements, wrinkle number counting, wrinkle density counting, etc. For example, the surface profile of pores shown in FIG. 3E allows more accurate pore size measurements. Similarly, the surface profile of a wrinkle shown in FIG. 3D allows more accurate wrinkle length and depth measurements.

In some embodiments, the surface profile is analyzed to identify at least one skin condition by comparing pixel values to predetermined criteria associated with various skin conditions. Conditions associated with the skin that may be detected and classified include, but are not limited to, enlarged pores, roughness variation, emerging lines, fine lines, wrinkles, pore health.

In addition, color images may be used in conjunction to detect and classify, for example, skin tone/color, pigment evenness, pigment darkness, diffuse redness (e.g., indicative of sensitive or reactive skin), intense localized red levels (e.g., indicative of vascular lesions/telangiectasias), radiance intensity, UV damage, pore health, hydration levels, collagen content, skin type, topical inflammation or recent ablation, keratosis, deeper inflammation, sun spots, different kinds of pigmentation including freckles, moles, growths, undereye circles, scars, acne, fungi, erythema and other artifacts. Images may be used to perform feature measurements, such as the size or volume of a lip, nose, eyes, ears, chin, cheeks, forehead, eyebrows, teeth, or other features. Other examples of feature measurements include spot counts, and measurement of the length, thickness and/or curvature of an eyelash. Image pixels may be used to characterize lip conditions, which may include, without limitation, lip surface area, and color. A combination the surface profile and color images may be used to characterize fine lines, wrinkles, and/or characteristics associated with lip edge demarcation. Characteristics associated with lip edge demarcation may include, for example, color contrast, line roughness, and color variation.

In some embodiments, to analyze either skin pixels or non-skin pixels (e.g., pixels corresponding to hair, clothing, eyes, lips, etc.) in surface or sub-surface skin images, pixels are analyzed on a pixel-by-pixel basis to distinguish skin pixels from non-skin pixels. Identification of skin and non-skin pixels is described, for example, in U.S. Pat. No. 7,454,046, entitled "Method and System for Analyzing Skin Conditions Using Digital Images," issued Nov. 18, 2008, which is incorporated by reference herein in its entirety. For example, assuming the pixels have red, green, and blue sub-pixels with pixel values that range between 0-255, pixels with red channel values in the range of 105-255, green channel values in the range of 52-191, and blue channel values in the range of 32-180 are identified as skin pixels. Furthermore, in some embodiments a pre-stored template or coordinate reference is used to define certain pixels as non-skin pixels and a skin map or skin mask may be used to define certain pixels as non-skin pixels, as described in U.S. Pat. No. 7,454,046 in accordance with some embodiments.

In some embodiments, the surface profile is compared with old (i.e., historical) images to identify variations in skin conditions and/or features over time. For example, a newly generated image may be displayed next to a stored historical image in a user interface (e.g., UI 234, FIG. 2A). In some embodiments, a computer system (e.g., the computer 226, FIG. 2A) performs automated comparison of one or more newly generated images with one or more historical images to track changes in skin conditions and features. For example, the system calculates changes in size of features (e.g., pores and/or wrinkles) on the skin. Results of this automated comparison are displayed in a user interface (e.g., UI 234, FIG. 2A).

When comparing multiple images, the images are first aligned to allow the same features to be identified in the multiple images. In some embodiments, images are aligned using a three-point selection process that identifies points in the center of the eyes and the center of the lips and aligns the images accordingly. In some embodiments, images are aligned using an automated facial detection and recognition software application or a set of instructions that identifies a plurality of distinct points on each facial profile (e.g., 50 points or more).

In some embodiments, the system transmits a recommendation to a cosmetic formulation control system coupled to an automated cosmetic formulator. The recommendation is typically based on the variations in skin conditions and/or features over time. The formulator then prepares the recommended product in real time, thus providing the subject with a customized cosmetic product based on the recommendation. In some embodiments, the system and cosmetic formulation control system are integrated into a single system. The cosmetic formulation control system is described in detail in U.S. patent application Ser. No. 13/078,834, filed Apr. 1, 2011, entitled "Methods and Systems for Imaging and Modeling Skin Using Polarized Lighting," which is incorporated by reference herein in its entirety. In some embodiments, the formulator includes an automated dispenser which dispenses the cosmetics in accordance with the instructions from the cosmetic formulation control system.

The foregoing description, for purpose of explanation, has been described with reference to specific embodiments. However, the illustrative discussions above are not intended to be exhaustive or to limit the inventions to the precise forms disclosed. Many modifications and variations are possible in view of the above teachings. The embodiments were chosen and described in order to best explain the principles of the inventions and their practical applications, to thereby enable others skilled in the art to best utilize the inventions and various embodiments with various modifications as are suited to the particular use contemplated.

What is claimed is:

1. A method, comprising:
   illuminating a subject with light from a plurality of light sources, the plurality of light sources having distinct colors and configured to illuminate the subject from distinct locations, wherein the plurality of light sources includes light sources of at least two distinct colors;

obtaining a multi-color image of the subject, the multi-color image comprising respective values corresponding to respective intensities of light of respective colors for each region of the subject; and determining a surface profile of the subject in accordance with the respective values corresponding to the respective intensities of light of the respective colors, wherein determining the surface profile of the subject includes:
  segmenting a surface of the subject into a plurality of regions; and
  determining an orientation of each region of at least a subset of the plurality of regions, wherein determining the orientation of each region includes comparing a first intensity of light of a first color reflected from the region and a second intensity of light of a second color reflected from the region.

2. The method of claim 1, wherein obtaining the multi-color image includes:
  obtaining a parallel-polarization image of the subject;
  obtaining a cross-polarization image of the subject; and
  subtracting the cross-polarization image of the subject from the parallel-polarization image of the subject to produce the multi-color image of the subject.

3. The method of claim 1, wherein determining the orientation of each region includes:
  determining respective intensities of light, corresponding to respective light sources of the plurality of light sources, reflected from the region; and
  comparing the respective intensities of light reflected from the region.

4. The method of claim 1, including:
  determining the surface profile of at least a portion of the subject based on the orientations of the subset of regions.

5. The method of claim 1, wherein:
  the plurality of light sources includes light sources of at least four distinct colors; and
  determining the orientation of each region includes:
    determining a first angle of the region by comparing a first intensity of light of a first color reflected from the region and a second intensity of light of a second color reflected from the region;
    determining a second angle of the region by comparing a third intensity of light of a third color reflected from the region and a fourth intensity of light of a fourth color reflected from the region; and
    determining the orientation of the region by combining the first angle and the second angle.

6. The method of claim 1, further comprising:
  combining the surface profile of the subject with a three-dimensional model of the subject.

7. The method of claim 1, further comprising:
  updating a three-dimensional model of the subject in accordance with the surface profile of the subject.

8. The method of claim 1, wherein the plurality of light sources emits light of respective colors that have distinct spectra.

9. An optical system, comprising:
  a plurality of light sources for illuminating a subject, the plurality of light sources having distinct colors and configured to illuminate the subject from distinct locations, wherein the plurality of light sources includes light sources of at least two distinct colors;
  an optical image sensor used for obtaining a multi-color image of the subject, the multi-color image comprising respective values corresponding to respective intensities of light of respective colors for each region of the subject;
  one or more processors coupled with the optical image sensor; and
  memory storing one or more programs for execution by the one or more processors, the one or more programs including instructions for determining a surface profile of the subject in accordance with the respective values corresponding to the respective intensities of light of the respective colors, wherein determining the surface profile of the subject includes:
    segmenting a surface of the subject into a plurality of regions; and
    determining an orientation of each region of at least a subset of the plurality of regions, wherein determining the orientation of each region includes comparing a first intensity of light of a first color reflected from the region and a second intensity of light of a second color reflected from the region.

10. The optical system of claim 9, further comprising a rotatably mounted polarizer coupled with the one or more processors, wherein the one or more programs include instructions for:
  obtaining a parallel-polarization image of the subject;
  obtaining a cross-polarization image of the subject; and
  subtracting the cross-polarization image of the subject from the parallel-polarization image of the subject to produce the multi-color image of the subject.

11. The optical system of claim 9, wherein the instructions for determining the orientation of each region include:
  determining respective intensities of light, corresponding to respective light sources of the plurality of light sources, reflected from the region; and
  comparing the respective intensities of light reflected from the region.

12. The optical system of claim 9, wherein:
  the plurality of light sources includes light sources of at least four distinct colors; and
  the instructions for determining the orientation of each region include instructions for:
    determining a first angle of the region by comparing a first intensity of light of a first color reflected from the region and a second intensity of light of a second color reflected from the region;
    determining a second angle of the region by comparing a third intensity of light of a third color reflected from the region and a fourth intensity of light of a fourth color reflected from the region; and
    determining the orientation of the region by combining the first angle and the second angle.

13. A non-transitory computer readable storage medium storing one or more programs for execution by one or more processors of a computer system, the one or more programs including instructions for:
  obtaining a multi-color image of a subject illuminated with a plurality of light sources that has distinct colors and is configured to illuminate the subject from distinct locations, wherein the plurality of light sources includes light sources of at least two distinct colors, the multi-color image comprising respective values corresponding to respective intensities of light of respective colors for each region of the subject; and
  determining a surface profile of the subject in accordance with the respective values corresponding to the respective intensities of light of the respective colors, wherein determining the surface profile of the subject includes:

segmenting a surface of the subject into a plurality of regions; and determining an orientation of each region of at least a subset of the plurality of regions, wherein determining the orientation of each region includes comparing a first intensity of light of a first color reflected from the region and a second intensity of light of a second color reflected from the region.

14. The computer readable storage medium of claim 13, wherein the one or more programs include instructions for:

obtaining a parallel-polarization image of the subject;

obtaining a cross-polarization image of the subject; and subtracting the cross-polarization image of the subject from the parallel-polarization image of the subject to produce the multi-color image of the subject.

15. The computer readable storage medium of claim 13, wherein the instructions for determining the orientation of each region include:

determining respective intensities of light, corresponding to respective light sources of the plurality of light sources, reflected from the region; and comparing the respective intensities of light reflected from the region.

16. The computer readable storage medium of claim 13, wherein:

the plurality of light sources includes light sources of at least four distinct colors; and the instructions for determining the orientation of each region include instructions for:

determining a first angle of the region by comparing a first intensity of light of a first color reflected from the region and a second intensity of light of a second color reflected from the region;

determining a second angle of the region by comparing a third intensity of light of a third color reflected from the region and a fourth intensity of light of a fourth color reflected from the region; and determining the orientation of the region by combining the first angle and the second angle.

* * * * *